US009902676B2

(12) United States Patent
Becker et al.

(10) Patent No.: US 9,902,676 B2
(45) Date of Patent: Feb. 27, 2018

(54) PROCESS FOR MAKING CYCLOHEXANONE

(71) Applicant: ExxonMobil Chemical Patents Inc., Baytown, TX (US)

(72) Inventors: Christopher L. Becker, Manhattan, KS (US); Jason D. Davis, Zachary, LA (US); Jihad M. Dakka, Whitehouse Station, NJ (US); Kirk C. Nadler, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/324,671

(22) PCT Filed: Aug. 3, 2015

(86) PCT No.: PCT/US2015/043491
§ 371 (c)(1),
(2) Date: Jan. 6, 2017

(87) PCT Pub. No.: WO2016/025219
PCT Pub. Date: Feb. 18, 2016

(65) Prior Publication Data
US 2017/0204037 A1    Jul. 20, 2017

Related U.S. Application Data

(60) Provisional application No. 62/037,824, filed on Aug. 15, 2014, provisional application No. 62/037,801, filed on Aug. 15, 2014, provisional application No. 62/037,814, filed on Aug. 15, 2014, provisional application No. 62/037,794, filed on Aug. 15, 2014, provisional application No. 62/057,919, filed on Sep. 30, 2014.

(30) Foreign Application Priority Data

Jan. 16, 2015 (EP) .................................... 15151424

(51) Int. Cl.
*C07C 45/82* (2006.01)
(52) U.S. Cl.
CPC .................................... *C07C 45/82* (2013.01)
(58) Field of Classification Search
CPC ....................................................... C07C 45/82
USPC ................................................. 568/366, 798
See application file for complete search history.

(56) References Cited

U.S. PATENT DOCUMENTS

| 4,169,857 | A | 10/1979 | Murtha |
| 4,200,553 | A | 4/1980 | Van Peppen et al. |
| 5,233,095 | A | 8/1993 | Fellmann et al. |
| 6,037,513 | A | 3/2000 | Chang et al. |
| 7,579,506 | B2 | 8/2009 | Leconte et al. |
| 8,921,603 | B2 | 12/2014 | Kuechler et al. |
| 9,169,175 | B2 | 10/2015 | Kuechler et al. |
| 2011/0021844 | A1 | 1/2011 | Dakka et al. |
| 2012/0302799 | A1 | 11/2012 | Dakka et al. |
| 2013/0217922 | A1 | 8/2013 | Kuechler et al. |
| 2017/0152201 | A1 | 6/2017 | Becker et al. |
| 2017/0204033 | A1 | 7/2017 | Becker et al. |
| 2017/0204034 | A1 | 7/2017 | Becker et al. |
| 2017/0204035 | A1 | 7/2017 | Becker et al. |
| 2017/0275226 | A1 | 9/2017 | Kuechler et al. |
| 2017/0283353 | A1 | 10/2017 | Becker et al. |

FOREIGN PATENT DOCUMENTS

| CN | 102015588 | 4/2011 |
| CN | 102015604 | 4/2011 |
| CN | 103664558 | 3/2014 |
| TW | 201619109 | 6/2016 |
| TW | 201619110 | 6/2016 |
| WO | 2009/025939 A | 2/2009 |
| WO | 2009/058527 A | 5/2009 |
| WO | 2009/058531 A | 5/2009 |
| WO | 2009/128984 A | 10/2009 |
| WO | 2009/131769 A | 10/2009 |
| WO | WO2009/134514 | 11/2009 |
| WO | WO2011/001244 | 1/2011 |
| WO | WO2011/096993 | 8/2011 |
| WO | 2012/036828 A | 3/2012 |
| WO | WO2012/036819 | 3/2012 |
| WO | WO2014/042993 | 3/2014 |
| WO | 2013/165659 A | 5/2014 |
| WO | 2014/081597 A | 5/2014 |
| WO | WO2016/025214 | 2/2016 |
| WO | WO2016/025217 | 2/2016 |
| WO | WO2016/025218 | 2/2016 |
| WO | 2017/019196 A | 2/2017 |
| WO | 2017/023429 A | 2/2017 |
| WO | 2017/023430 A | 2/2017 |

OTHER PUBLICATIONS

Van Peppen, J.F. et al., "Phenol Hydrogenation Process", Catalysis of Organic Reactions, pp. 355-372, 1985.
Schmidt, Robert J., "Industrial Catalytic Process-Phenol Production", Applied Catalysis A: General, vol. 280, pp. 89-103, 2005.

*Primary Examiner* — Sikarl Witherspoon

(57) ABSTRACT

Disclosed are processes for making cyclohexanone from a mixture comprising phenol, cyclohexanone, cyclohexylbenzene, and a catalyst poison component, comprising a step of removing at least a portion of the catalyst poison component to reduce poisoning of a hydrogenation catalyst used for hydrogenating phenol to cyclohexanone.

25 Claims, 7 Drawing Sheets

PROCESS FOR MAKING CYCLOHEXANONE

PRIORITY CLAIM

This application is a National Stage Application of International Application No. PCT/US2015/043491 filed Aug. 3, 2015, which claims priority to U.S. Provisional Application Ser. No. 62/057,919 filed Sep. 30, 2014; U.S. Provisional Application Ser. No. 62/037,794 filed Aug. 15, 2014; U.S. Provisional Application Ser. No. 62/037,801 filed Aug. 15, 2014; U.S. Provisional Application Ser. No. 62/037,814 filed Aug. 15, 2014; U.S. Provisional Application Ser. No. 62/037,824 filed Aug. 15, 2014 and European Application No. 15151424.7 filed Jan. 16, 2015, the disclosures of which are fully incorporated herein by their reference.

FIELD

The present invention relates to processes for making cyclohexanone. In particular, the present invention relates to processes for making cyclohexanone by phenol hydrogenation. The present invention is useful, e.g., in making cyclohexanone from cyclohexylbenzene oxidation and cyclohexylbenzene hydroperoxide cleavage.

BACKGROUND

Cyclohexanone is an important material in the chemical industry and is widely used in, for example, production of phenolic resins, bisphenol A, ε-caprolactam, adipic acid, and plasticizers. One method for making cyclohexanone is by hydrogenating phenol.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. The separated phenol product can then be converted to cyclohexanone by a step of hydrogenation.

It is known from, e.g., U.S. Pat. No. 6,037,513, that cyclohexylbenzene can be produced by contacting benzene with hydrogen in the presence of a bifunctional catalyst comprising a molecular sieve of the MCM-22 type and at least one hydrogenation metal selected from palladium, ruthenium, nickel, cobalt, and mixtures thereof. This reference also discloses that the resultant cyclohexylbenzene can be oxidized to the corresponding hydroperoxide, which can then be cleaved to produce a cleavage mixture of phenol and cyclohexanone, which, in turn, can be separated to obtain pure, substantially equimolar phenol and cyclohexanone products. This cyclohexylbenzene-based process for co-producing phenol and cyclohexanone can be highly efficient in making these two important industrial materials. Given the higher commercial value of cyclohexanone than phenol, it is highly desirable that in this process more cyclohexanone than phenol be produced. While this can be achieved by subsequently hydrogenating the pure phenol product produced in this process to covert a part or all of the phenol to cyclohexanone, a more economical process and system would be highly desirable.

One solution to making more cyclohexanone than phenol from the above cyclohexylbenzene-based process is to hydrogenate a mixture containing phenol and cyclohexanone obtained from the cleavage mixture to convert at least a portion of the phenol contained therein to cyclohexanone. However, because the phenol/cyclohexanone mixture invariably contains non-negligible amounts of (i) catalyst poison component(s) that can poison the hydrogenation catalyst, and (ii) cyclohexylbenzene that can be converted to bicyclohexane in the hydrogenation step, and because hydrogenation of the phenol/cyclohexanone/cyclohexylbenzene mixture can also lead to the formation of cyclohexanol, resulting in yield loss, this process is not without challenge.

As such, there is a need for an improved process for making cyclohexanone from a mixture containing phenol, cyclohexanone, cyclohexylbenzene, and catalyst poison component(s).

The present invention satisfies this and other needs.

SUMMARY

It has been found that catalyst poison components contained in phenol/cyclohexanone mixtures can be effectively removed by using an anterior stripper distillation column and/or sorbent(s) before the primary fractionation column for separating cyclohexanone from the phenol/cyclohexanone mixture, and/or by using a posterior stripper distillation column and/or sorbent(s) after the primary fractionation column but before the hydrogenation reactor, thereby alleviating the poisoning of the hydrogenation catalyst.

In a first aspect, the present disclosure relates to a process for making cyclohexanone, the process comprising: (I) feeding a first mixture comprising cyclohexanone, phenol, cyclohexylbenzene, and a catalyst poison component into a first distillation column; (II) obtaining from the first distillation column: (i) a first upper effluent comprising cyclohexanone at a concentration higher than the first mixture and a portion of the catalyst poison component; (ii) a first middle effluent comprising cyclohexanone, phenol at a concentration higher than the first mixture, cyclohexylbenzene, bicyclohexane, and a portion of the catalyst poison component; and (iii) a first lower effluent comprising cyclohexylbenzene at a concentration higher than the first mixture; (III) removing at least a portion of the catalyst poison component from the first middle effluent to obtain a hydrogenation feed; (IV) feeding at least a portion of the hydrogenation feed and hydrogen into a hydrogenation reaction zone where phenol reacts with hydrogen in the presence of a hydrogenation catalyst under hydrogenation reaction conditions to obtain a hydrogenation reaction product comprising cyclohexanone at a concentration higher than the hydrogenation feed, phenol at a concentration lower than the hydrogenation feed, cyclohexylbenzene, and bicyclohexane; and (V) feeding at least a portion of the hydrogenation reaction product into the first distillation column. The hydrogenation catalyst poison component, which may comprise a light component having a normal boiling point lower than cyclohexanone, is capable of reducing the activity of the hydrogenation catalyst if it is allowed to contact the hydrogenation catalyst under the hydrogenation reaction conditions. In this process, at least a portion of the catalyst poison component is removed by using a posterior removal mechanism located after the primary fractionation column but before the hydrogenation reaction zone.

In a second aspect, the present disclosure relates to a process for making cyclohexanone, the process comprising: (I) feeding a first mixture comprising cyclohexanone, phenol, and cyclohexylbenzene into a first distillation column, wherein the first mixture is provided by removing at least a portion of a catalyst poison component from a crude mixture comprising cyclohexanone, phenol, cyclohexylbenzene, and the catalyst poison component; (II) obtaining from the first distillation column: (i) a first upper effluent comprising cyclohexanone at a concentration higher than the first mixture; (ii) a first middle effluent comprising cyclohexanone, phenol at a concentration higher than the first mixture, cyclohexylbenzene, bicyclohexane, and optionally a portion of the catalyst poison component; and (iii) a first lower effluent comprising cyclohexylbenzene at a concentration higher than the first mixture; (III) providing a hydrogenation feed from at least a portion of the first middle effluent; (IV) feeding at least a portion of the hydrogenation feed and hydrogen into a hydrogenation reaction zone where phenol reacts with hydrogen in the presence of a hydrogenation catalyst under hydrogenation reaction conditions to obtain a hydrogenation reaction product comprising cyclohexanone at a concentration higher than the hydrogenation feed, phenol at a concentration lower than the hydrogenation feed, cyclohexylbenzene, and bicyclohexane; and (V) feeding at least a portion of the hydrogenation reaction product into the first distillation column, wherein the hydrogenation catalyst poison component is capable of reducing the activity of the hydrogenation catalyst if the catalyst poison component is allowed to contact the hydrogenation catalyst under the hydrogenation reaction conditions. In this process, at least a portion of the catalyst poison component is removed by using an anterior removal mechanism located before the primary fractionation column.

In a specific embodiment of either the first or the second aspect of the processes of the present invention, both an anterior removal mechanism and a posterior removal mechanism is employed to remove at least a portion of the catalyst poison component from the hydrogenation feed.

DETAILED DESCRIPTION

Figure 1:
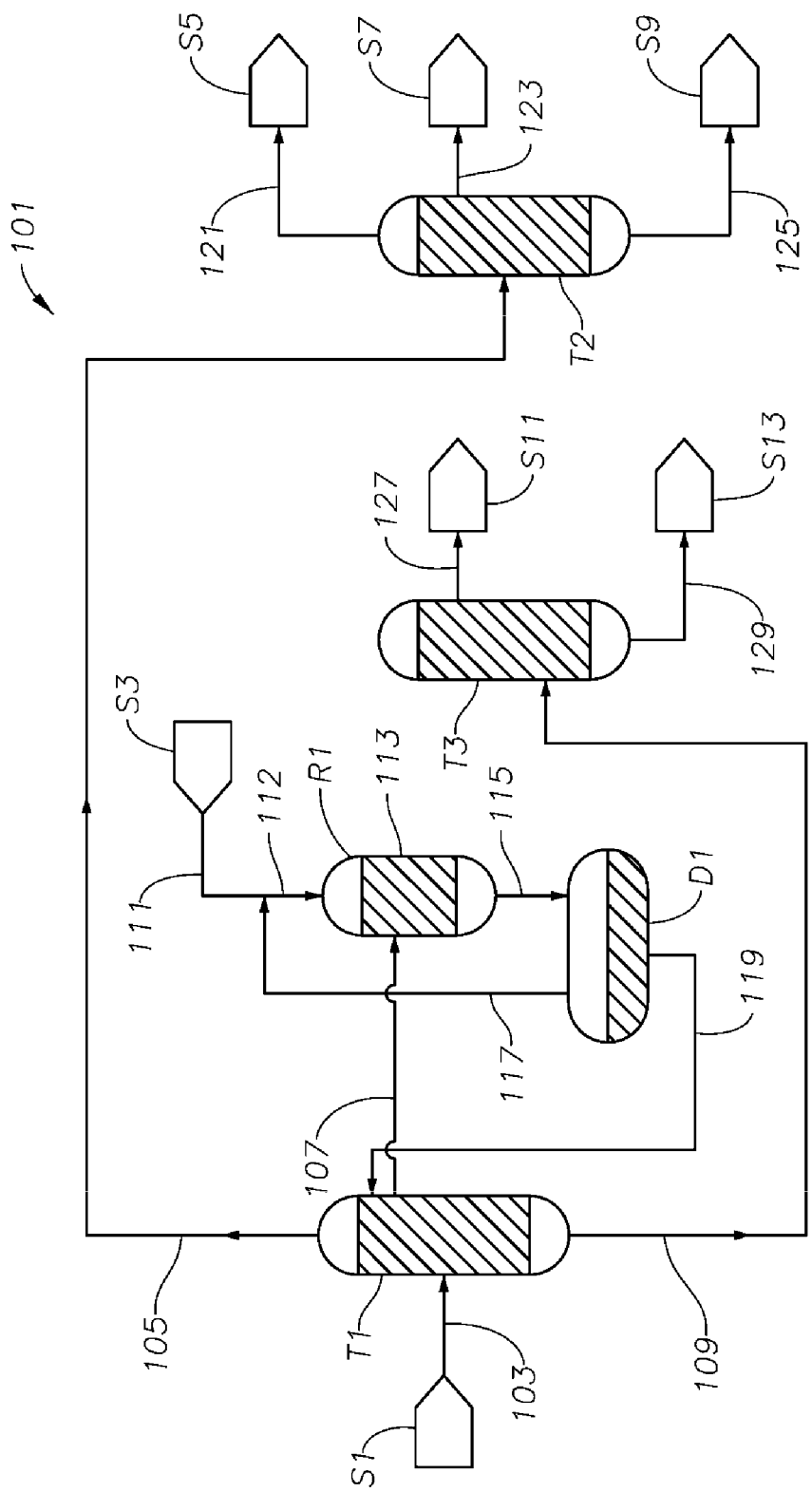
FIG. 1 is a schematic diagram showing a process/system for making cyclohexanone from a first mixture comprising phenol, cyclohexanone and cyclohexylbenzene including a primary fractionation column T1, a hydrogenation reactor R1, and a cyclohexanone purification column T2.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments comprising "a light component" include embodiments where one, two or more light components exist, unless specified to the contrary or the context clearly indicates that only one light component exists.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first feedstock are expressed based on the total weight of the first feedstock. All ranges expressed herein should include both end points as two specific embodiments unless specified or indicated to the contrary.

In the present disclosure, a location "in the vicinity of" an end (top or bottom) of a column means a location within a distance of a*Hc from the end (top or bottom) of the column, where Hc is the height of the column from the bottom to the top, and a1≤a≤a2, where a1 and a2 can be, independently: 0, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, as long as a1<a2. For example, a location in the vicinity of an end of a column can have an absolute distance from the end (top or bottom) of at most D meters, where D can be 5.0, 4.5, 4.0, 3.5, 3.0, 2.5, 2.0, 1.5, 1.0, 0.8, 0.5, 0.4, 0.3, 0.2, 0.1, or 0.

An "upper effluent" as used herein may be at the very top or the side of a vessel such as a fractionation column or a reactor, with or without an additional effluent above it. Preferably, an upper effluent is drawn at a location in the vicinity of the top of the column. Preferably, an upper effluent is drawn at a location above at least one feed. A "lower effluent" as used herein is at a location lower than the upper effluent, which may be at the very bottom or the side of a vessel, and if at the side, with or without additional effluent below it. Preferably, a lower effluent is drawn at a location in the vicinity of the bottom of the column. Preferably, a lower effluent is drawn at a location below at least one feed. As used herein, a "middle effluent" is an effluent between an upper effluent and a lower effluent. The "same level" on a distillation column means a continuous segment of the column with a total height no more than 5% of the total height of the column.

As used herein, the conversion of a reactant Re1 and the selectivity of a given product Pro1 in a given reaction system is calculated as follows. Assuming that a total of $n_0$ moles of Re1 is charged into the reaction system, the net effect of the process results in $n_1$ moles of Re1 converted to Pro1, and the reaction mixture exiting the reaction system comprises $n_2$ moles of residual Re1, then the overall conversion of Re1 (Con(Re1)) and the selectivity toward Pro1 (Sel(Pro1)) is obtained as follows:

$$Con(Re1) = \frac{n_0 - n_2}{n_0} \times 100\%,$$

and $$Sel(Re1) = \frac{n_1}{n_0 - n_2} \times 100\%.$$

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

As used herein, the term "methylcyclopentanone" includes both isomers 2-methylcyclopentanone (CAS Registry No. 1120-72-5) and 3-methylcyclopentanone (CAS Registry No. 1757-42-2), at any proportion between them, unless it is clearly specified to mean only one of these two isomers or the context clearly indicates that is the case. It should be noted that under the conditions of the various steps of the present processes, the two isomers may undergo isomerization reactions to result in a ratio between them different from that in the raw materials immediately before being charged into a vessel such as a fractionation column.

As used herein, the generic term "dicyclohexylbenzene" ("DiCHB") includes, in the aggregate, 1,2-dicyclohexylbenzene, 1,3-dicyclohexylbenzene, and 1,4-dicyclohexylbenzene, unless clearly specified to mean only one or two thereof. The term cyclohexylbenzene, when used in the singular form, means mono substituted cyclohexylbenzene. As used herein, the term "C12" means compounds having 12 carbon atoms, and "C12+ components" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding oxygenates such as alcohols, ketones, acids, and esters derived from these compounds. As used herein, the term "C18" means compounds having 18 carbon atoms, and the term "C18+ components" means compounds having at least 18 carbon atoms. Examples of C18+ components include, among others, diicyclohexylbenzenes ("DiCHB," described above), tricyclohexylbenzenes ("TriCHB," including all isomers thereof, including 1,2,3-tricyclohexylbenzene, 1,2,4-tricyclohexylbenzene, 1,3,5-tricyclohexylbenzene, and mixtures of two or more thereof at any proportion). As used herein, the term "C24" means compounds having 24 carbon atoms.

As used herein, the term "light component" means compound having a normal boiling point (i.e., boiling point at a pressure of 101,325 Pa) lower than cyclohexanone. Examples of the light component include, but are not limited to: (i) methylcyclopentanone; (ii) water; (iii) hydrocarbons comprising 4, 5, 6, 7, 8, 9, 10, 11, or 12 carbon atoms, including but not limited to linear, branched linear, cyclic, substituted cyclic, alkanes, alkenes, and dienes; (iv) oxygenates such as alcohols, aldehydes, ketones, carboxylic acids, ethers, and the like, of hydrocarbons; (v) N-containing compounds, such as amines, amides, imides, $NO_2$-substituted compounds, and the like; (vi) S-containing compounds, such as sulfides, sulfites, sulfates, sulfones, and the like. It has been found that S-containing compounds, N-containing compounds, dienes, alkenes, cyclic alkenes, and cyclic dienes, and carboxylic acids comprising 1, 2, 3, 4, 5, 6, 7, or 8 carbon atoms can be present in the phenol/cyclohexanone mixture produced by hydroperoxide cleavage reactions described in greater detail below, and they can be particularly detrimental to the performance of the hydrogenation catalyst, leading to catalyst poisoning and undesirable, premature catalyst performance reduction.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve used in the catalyst of the present disclosure is selected from (a) MCM-49; (b) MCM-56; and (c) isotypes of MCM-49 and MCM-56, such as ITQ-2.

The process and systems for making cyclohexanone disclosed herein can be advantageously used for making cyclohexanone from any feed mixture comprising phenol, cyclohexanone and cyclohexylbenzene. While the feed may be derived from any process or source, it is preferably obtained from the acid cleavage of a mixture comprising cyclohexylbenzene hydroperoxide and cyclohexylbenzene, which, in turn, is preferably obtained from aerobic oxidation of cyclohexylbenzene, which, in turn, is preferably obtained benzene. Steps of these preferred processes are described in detail below.

Supply of Cyclohexylbenzene

The cyclohexylbenzene supplied to the oxidation step can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

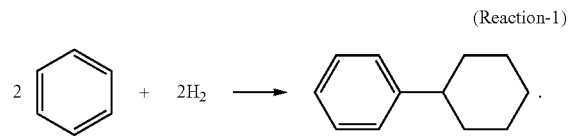 [SMILES: c1ccccc1 ; c1ccc(C2CCCCC2)cc1]

(Reaction-1)

Alternatively, cyclohexylbenzene can be produced by direct alkylation of benzene with cyclohexene in the presence of a solid-acid catalyst such as molecular sieves in the MCM-22 family according to the following Reaction-2:

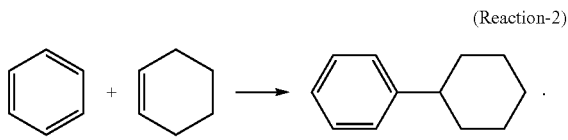

(Reaction-2)

U.S. Pat. Nos. 6,730,625; 7,579,511, and International Patent Applications WO2009/131769, and WO 2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include Pd, Pt, Rh, Ru, Ir, Ni, Zn, Sn, Co, with Pd being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials and/or binders. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, SnO, $SnO_2$, and mixtures, combinations and complexes thereof.

The effluent from the hydroalkylation reaction (hydroalkylation reaction product mixture) or from the alkylation reaction (alkylation reaction product mixture) may contain some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step.

Depending on the quantity of the heavies fraction, it may be desirable to either (a) transalkylate the C18s such as DiCHB and C24s such as TriCHB with additional benzene or (b) dealkylate the C18s and C24s to maximize the production of the desired monoalkylated species.

Transalkylation with additional benzene is desirably effected in a transalkylation reactor, which is separate from the hydroalkylation reactor, over a suitable transalkylation catalyst, such as a molecular sieve of the MCM-22 type, zeolite beta, MCM-68 (see U.S. Pat. No. 6,049,018), zeolite Y, zeolite USY, and mordenite. The transalkylation reaction is desirably conducted under at least partially liquid phase conditions, which suitably include a temperature in the range from 100° C. to 300° C., a pressure in the range from 800 kPa to 3500 kPa, a weight hourly space velocity from 1 hr$^{-1}$ to 10 hr$^{-1}$ on total feed, and a benzene/dicyclohexylbenzene weight ratio in a range from 1:1 to 5:1.

Dealkylation is also desirably effected in a reactor separate from the hydroalkylation reactor, such as a reactive distillation unit, at a temperature of about 150° C. to about 500° C. and a pressure in a range from 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as WO$_x$/ZrO$_2$, phosphoric acid, sulfated zirconia and mixtures thereof. Desirably, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction can be from 0 to about 0.9, such as from about 0.01 to about 0.5. Similarly, although the dealkylation reaction can be conducted in the absence of added hydrogen, hydrogen is desirably introduced into the dealkylation reactor to assist in coke reduction. Suitable hydrogen addition rates are such that the molar ratio of hydrogen to poly-alkylated aromatic compound in the total feed to the dealkylation reactor can be from about 0.01 to about 10.

The transalkylation or dealkylation product mixture comprising benzene, C12s and heavies can then be separated to obtain a C6 fraction, which comprises primarily benzene and can be recycled to the hydroalkylation/alkylation step, a C12s fraction comprising primarily cyclohexylbenzene, and a heavies fraction which can be subjected to a transalkylation/dealkylation reaction again or discarded.

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

The cyclohexylbenzene feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) water at a concentration up to 5000 ppm, such as from 100 ppm to 1000 ppm; and (iv) olefins or alkene benzenes, such as phenylcyclohexene, at a concentration no greater than 1000 ppm.

Oxidation of Cyclohexylbenzene

In the oxidation step, at least a portion of the cyclohexylbenzene contained in the oxidation feed is converted to cyclohexyl-1-phenyl-1-hydroperoxide, the desired hydroperoxide, according to the following Reaction-3:

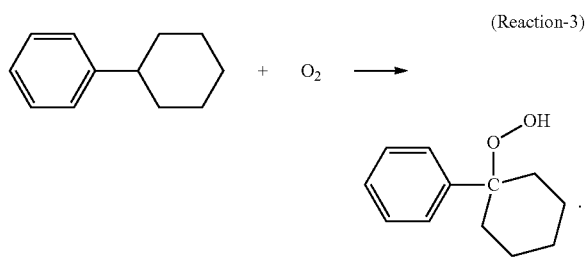
(Reaction-3)

In exemplary processes, the oxidizing step may be accomplished by contacting an oxygen-containing gas, such as air and various derivatives of air, with the feed comprising cyclohexylbenzene. For example, a stream of pure O2, O2 diluted by inert gas such as N2, pure air, or other O2-containing mixtures can be pumped through the cyclohexylbenzene-containing feed in an oxidation reactor.

The oxidation may be conducted in the absence or presence of a catalyst. Examples of suitable oxidation catalysts include those having a structure of formula (FC-I), (FC-II), or (FC-III) below:

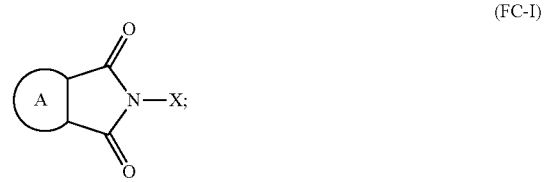
(FC-I)

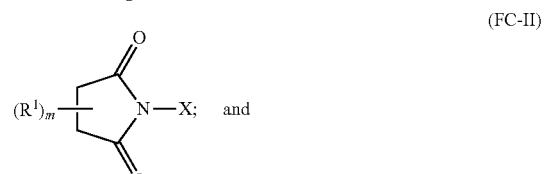
(FC-II)

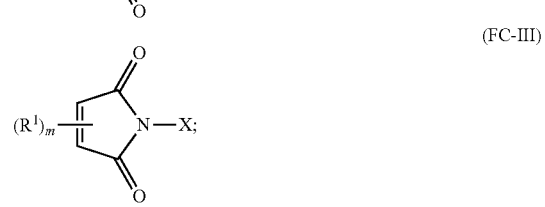
(FC-III)

where:

A represents a ring optionally comprising a nitrogen, sulfur, or oxygen in the ring structure, and optionally substituted by an alkyl, an alkenyl, a halogen, or a N-, S-, or O-containing group or other group;

X represents a hydrogen, an oxygen free radical, a hydroxyl group, or a halogen;

R[1], the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1 or 2.

Examples of particularly suitable catalysts for the oxidation step include those represented by the following formula (FC-IV):

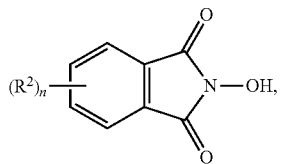

where:

R[2], the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

One especially suitable catalyst having the above formula (FC-IV) for the oxidation step is NHPI (N-hydroxyphthalimide). For example, the feed to the oxidizing step can comprise from 10 to 2500 ppm of NHPI by weight of the cyclohexylbenzene in the feed.

Other non-limiting examples of the oxidation catalyst include: 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy (pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, N-hydroxy-o-benzenedisulphonimide, and N,N',N''-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N''-trihydroxyisocyanuric acid is employed in an amount from 0.0001 wt % to 15 wt %, such as from 0.001 wt % to 5 wt %, of the cyclohexylbenzene feed.

Non-limiting examples of suitable reaction conditions of the oxidizing step include a temperature in a range from 70° C. to 200° C., such as 90° C. to 130° C., and a pressure in a range from 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing gas stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series and/or in parallel, each operating at the same or different conditions selected to enhance the oxidation reaction in the reaction media with different compositions. The oxidation reactor may be operated in a batch, semi-batch, or continuous flow manner well known to those skilled in the art.

Composition of the Oxidation Reaction Product Mixture

Desirably, the oxidation reaction product mixture exiting the oxidation reactor contains cyclohexyl-1-phenyl-1-hydroperoxide at a concentration in a range from Chp1 wt % to Chp2 wt %, based on the total weight of the oxidation reaction product mixture, where Chp1 and Chp2 can be, independently: 5, 10, 15, 20, 25, 30, 35, 40, 45, 50, 55, 60, 65, 70, 75, 80, as long as Chp1<Chp2. Preferably, the concentration of cyclohexyl-1-phenyl-1-hydroperoxide in the oxidation reaction product mixture is at least 20% by weight of the oxidation reaction product mixture. The oxidation reaction product mixture may further comprise residual cyclohexylbenzene at a concentration in a range from Cchb1 wt % to Cchb2 wt %, based on the total weight of the oxidation reaction product mixture, where Cchb1 and Cchb2 can be, independently: 20, 25, 30, 35, 40, 45, 50, 55, 60, 65, 70, 75, 80, 85, 90, 95, as long as Cchb1<Cchb2. Preferably, the concentration of cyclohexylbenzene in the oxidation reaction product mixture is at most 65% by weight of the oxidation reaction product mixture.

In addition, the oxidation reaction product mixture may contain one or more hydroperoxides other than cyclohexyl-1-phenyl-1-hydroperoxide generated as byproduct(s) of the oxidation reaction of cyclohexylbenzene, or as the oxidation reaction product of oxidizable component(s) other than cyclohexylbenzene that may have been contained in the feed supplied to the oxidizing step, such as cyclohexyl-2-phenyl-1-hydroperoxide, cyclohexyl-3-phenyl-1-hydroperoxide, and methylcyclopentylbenzene hydroperoxides. These undesired hydroperoxides are present at a total concentration from Cu1 wt % to Cu2 wt %, where Cu1 and Cu2 can be, independently: 0.1, 0.2, 0.3, 0.5, 0.7, 0.9, 1.0, 1.2, 1.4, 1.5, 1.6, 1.8, 2.0, 2.5, 3.0, 3.5, 4.0, 4.5, 5.0, 6.0, 7.0, 8.0, as long as Cu1<Cu2. They are undesirable because they may not convert into phenol and cyclohexanone in the cleavage reaction at the desired conversion and/or selectivity, resulting in overall yield loss.

As noted above, the oxidation reaction product mixture may also contain phenol as a further by-product of the oxidation reaction. The concentration of phenol (CPh) in the oxidation reaction product mixture exiting the oxidation reactor(s) can range from CPh1 ppm to CPh2 ppm, where CPh1 and CPh2 can be, independently: 50, 60, 70, 80, 90, 100, 150, 200, 250, 300, 350, 400, 450, 500, 550, 600, 650, 700, 750, 800, 850, 900, 950, 1000, 1500, 2000, as long as CPh1<CPh2.

The oxidation reaction product mixture may contain water. The concentration of water in the oxidation reaction product mixture exiting the oxidation reactor may range from C1a ppm to C1b ppm, based on the total weight of the oxidation reaction product mixture, where C1a and C1b can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as C1a<C1b.

The oxidation reaction product mixture may also contain part or all of any catalyst, such as NHPI, supplied to the oxidizing step. For example, the oxidation reaction product mixture may contain from 10 to 2500 ppm of NHPI, such as from 100 to 1500 ppm by weight of NHPI.

Treatment of the Oxidation Reaction Product Mixture

In the process of the present disclosure, before being supplied to the cleavage step, at least a portion of the oxidation reaction product mixture may be separated. The separation process may include subjecting at least a portion of the oxidation reaction product mixture to vacuum evaporation so as to recover: (i) a first fraction comprising the majority of the cyclohexyl-1-phenyl-1-hydroperoxide and other higher boiling components of the oxidation reaction product mixture, such as other hydroperoxides and NHPI catalyst, if present in the oxidation reaction product mixture portion; and (ii) a second fraction comprising a major portion of the cyclohexylbenzene, phenol, if any, and other lower boiling components of the oxidation reaction product mixture portion.

Desirably, in the first fraction, the concentration of cyclohexyl-1-phenyl-1-hydroperoxide can range from Cc1 wt % to Cc2 wt %, and the concentration of cyclohexylbenzene can range from Cd1 wt % to Cd2 wt %, based on the total weight of the first fraction, where Cc1 and Cc2 can be, independently: 40, 45, 50, 55, 60, 65, 70, 75, 80, 85, 90, as long as Cc1<Cc2; and Cd1 and Cd2 can be, independently: 10, 15, 20, 25, 30, 35, 40, 45, 50, as long as Cd1<Cd2.

Advantageously, in the second fraction, the concentration of cyclohexyl-1-phenyl-1-hydroperoxide can range from Cc3 wt % to Cc4 wt %, and the concentration of cyclohexylbenzene can range from Cd3 wt % to Cd4 wt %, based on the total weight of the second fraction, where Cc3 and Cc4 can be, independently: 0.01, 0.05, 0.10, 0.20, 0.40, 0.50, 0.60, 0.80, 1.00, 1.50, 2.00, 2.50, 3.00, 3.50, 4.00, 4.50, 5.00, as long as Cc3<Cc4; and Cd3 and Cd4 can be, independently: 90, 92, 94, 95, 96, 97, 98, or even 99, as long as Cd3<Cd4.

Because cyclohexylbenzene hydroperoxide is prone to decomposition at elevated temperatures, e.g., at above 150° C., the vacuum evaporation step to separate the oxidation reaction product mixture into the first and second fractions is conducted at a relatively low temperature, e.g., no higher than 130° C., or no higher than 120° C., or even no higher than 110° C. Cyclohexylbenzene has a high boiling point (239° C. at 101 kPa). Thus, at acceptable cyclohexylbenzene-removal temperatures, cyclohexylbenzene tends to have very low vapor pressure. Accordingly, preferably, to effectively remove a meaningful amount of cyclohexylbenzene from the oxidation reaction product mixture, the oxidation reaction product mixture is subjected to a very low absolute pressure, e.g., in a range from Pc1 kPa to Pc2 kPa, where Pc1 and Pc2 can be, independently: 0.05, 0.10, 0.15, 0.20, 0.25, 0.26, 0.30, 0.35, 0.40, 0.45, 0.50, 0.60, 0.65, 0.70, 0.75, 0.80, 0.85, 0.90, 0.95, 1.00, 1.50, 2.00, 2.50, 3.00, as long as Pc1<Pc2. Particularly advantageously, Pc1=0.25, and Pc2=1.5.

After separation of the oxidation reaction product mixture into the first and second fractions, part or all of the first fraction can be routed directly to the cleavage step. All or a portion of the first fraction may be cooled before passage to the cleavage step so as to cause crystallization of the unreacted imide oxidation catalyst. The imide crystals may then be recovered for reuse either by filtration or by scraping from a heat exchanger surface used to effect the crystallization.

The second fraction produced from the oxidation reaction product mixture may be treated to reduce the level of phenol therein before part or all of the cyclohexylbenzene in the second fraction is recycled to the hydrogenation.

Treatment of the second fraction can comprise contacting at least a portion of the second fraction with an aqueous composition comprising a base under conditions such that the base reacts with the phenol to produce a phenoate species which remains in the aqueous composition. A strong base, that is a base having a $pK_b$ value less than 3, such as less than 2, 1, 0, or −1, is desirably employed in the treatment of the second fraction. Particularly suitable bases include hydroxides of alkali metals (e.g., LiOH, NaOH, KOH, RbOH), hydroxides of alkaline earth metals ($Mg(OH)_2$, $Ca(OH)_2$, $Sr(OH)_2$, $Ba(OH)_2$), and mixtures of one or more thereof. Phenol can react with these hydroxides to form phenoates, which typically have higher solubility in water than phenol per se. A particularly desirable base is NaOH, which is cost efficient and capable of reacting with phenol in the second fraction to produce sodium phenoate. It should be noted that, when a hydroxide is used as the base, because of the reaction of $CO_2$ present in the atmosphere with the hydroxide, the aqueous composition may comprise, at various concentrations, one or more of a corresponding carbonate, bicarbonate, or carbonate-hydroxide complex. Desirably, the aqueous composition comprising the base has a pH of at least 8, preferably at least 10.

Contacting of the second fraction with the aqueous composition comprising a base produces an aqueous phase containing at least part of the phenol and/or a derivative thereof from the second fraction and an organic phase containing cyclohexylbenzene and having a reduced concentration of phenol as compared with the second fraction. Desirably, the phenol concentration in the organic phase is in the range from CPh7 ppm to CPh8 ppm, based on the total weight of the organic phase, where CPh7 and CPh8 can be, independently: 0, 10, 20, 30, 40, 50, 100, 150, 200, 250, as long as CPh7<CPh8.

The organic phase can then be separated from the aqueous phase, for example, spontaneously under gravity, and can then be recycled to the oxidizing step as a third fraction either directly, or more preferably, after water washing to remove base contained in the organic phase.

Cleavage Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-4:

(Reaction-4)

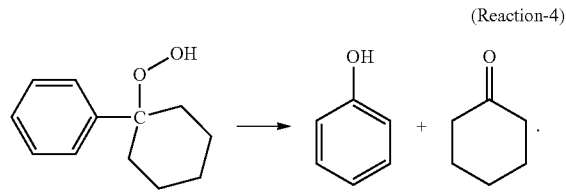 [SMILES: OOC1(c2ccccc2)CCCCC1 ; Oc1ccccc1 ; O=C1CCCCC1]

The cleavage product mixture may comprise the acid catalyst, phenol, cyclohexanone, cyclohexylbenzene, and contaminants.

The acid catalyst can be at least partially soluble in the cleavage reaction mixture, is stable at a temperature of at least 185° C. and has a lower volatility (higher normal boiling point) than cyclohexylbenzene.

Acid catalysts preferably include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

The cleavage reaction preferably occurs under cleavage conditions including a temperature in a range from 20° C. to 200° C., or from 40° C. to 120° C., and a pressure in a range from 1 to 370 psig (at least 7 kPa, gauge and no greater than 2,550 kPa, gauge), or from 14.5 psig to 145 psig (from 100 kPa, gauge to 1,000 kPa, gauge) such that the cleavage reaction mixture is completely or predominantly in the liquid phase during the cleavage reaction.

The cleavage reaction mixture can contain the acid catalyst at a concentration in a range from Cac1 ppm to Cac2 ppm by weight of the total weight of the cleavage reaction mixture, where Cac1 and Cac2 can be, independently: 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Preferably, Cac1 is 50, and Cac2 is 200.

Conversion of hydroperoxides, such as cyclohexyl-1-phenyl-1-hydroperoxide, and conveniently all cyclohexyl-1-phenyl-1-hydroperoxide and other hydroperoxides, may be very high in the cleavage reaction, e.g., at least AA wt %, where AA can be 90.0, 91.0, 92.0, 93.0, 94.0, 95.0, 96.0, 97.0, 98.0, 99.0, 99.5, 99.9, or even 100, the percentage based on the weight of a given hydroperoxide, or of all hydroperoxides fed to the cleavage step. This is desirable because any hydroperoxide, even the cyclohexyl-1-phenyl-1-hydroperoxide, becomes a contaminant in the downstream processes.

Desirably, each mole of cyclohexyl-1-phenyl-1-hydroperoxide produces one mole of phenol and one mole of cyclohexanone. However, due to side reactions, the selectivity of the cleavage reaction to phenol can range from Sph1% to Sph2% and the selectivity to cyclohexanone can range from Sch1% to Sch2%, where Sph1, Sph2, Sch1, and Sch2 can be, independently: 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation reaction product mixture, the cleavage reaction mixture may further comprise other added materials, such as the cleavage catalyst, a solvent, and one or more products of the cleavage reaction such as phenol and cyclohexanone recycled from the cleavage product mixture, or from a downstream separation step. Thus, the cleavage reaction mixture inside the cleavage reactor may comprise, based on the total weight of the cleavage reaction mixture: (i) phenol at a concentration from CPh9 wt % to CPh10 wt %, where CPh9 and CPh10 can be, independently: 20, 25, 30, 35, 40, 45, 50, 55, 60, 65, 70, 75, or 80, as long as CPh9<CPh10; (ii) cyclohexanone at a concentration from Cch1 wt % to Cch2 wt %, where Cch1 and Cch2 can be, independently: 20, 25, 30, 35, 40, 45, 50, 55, 60, 65, 70, 75, or 80, as long as Cch1<Cch2; and (iii) cyclohexylbenzene at a concentration from Cchb7 wt % to Cchb8 wt %, where Cchb7 and Cchb8 can be, independently: 5, 8, 9, 10, 12, 14, 15, 18, 20, 22, 24, 25, 26, 28, 30, 35, 40, 45, 50, 55, 60, 65, 70, as long as Cchb7<Cchb8.

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. The cleavage reactor may comprise a plurality of reactors in series, each performing a portion of the conversion reaction, optionally operating in different modes and at different conditions selected to enhance the cleavage reaction at the pertinent conversion range. The cleavage reactor can be a catalytic distillation unit.

The cleavage reactor can be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to at least a part of the heat generated.

The cleavage product mixture exiting the cleavage reactor may comprise, based on the total weight of the cleavage product mixture: (i) phenol at a concentration from CPh11 wt % to CPh12 wt %, where CPh11 and CPh12 can be, independently: 20, 25, 30, 35, 40, 45, 50, 55, 60, 65, 70, 75, or 80, as long as Ch11<CPh12; (ii) cyclohexanone at a concentration from Cch3 wt % to Cch4 wt %, where Cch3 and Cch4 can be, independently: 20, 25, 30, 35, 40, 45, 50, 55, 60, 65, 70, 75, or 80, as long as Cch3<Cch4; and (iii) cyclohexylbenzene at a concentration from Cchb9 wt % to Cchb10 wt %, where Cchb9 and Cchb10 can be, independently: 5, 8, 9, 10, 12, 14, 15, 18, 20, 22, 24, 25, 26, 28, 30, 35, 40, 45, 50, 55, 60, 65, 70, as long as Cchb9<Cchb10.

As discussed above, the cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO 2012/036822A1, the relevant content of which is incorporated herein by reference in its entirety.

At least a portion of the cleavage product mixture may be subjected to a neutralization reaction. Where a liquid acid such as sulfuric acid is used as the cleavage catalyst, it is highly desirable that the cleavage reaction product is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

Separation and Purification

A portion of the neutralized cleavage reaction product can then be separated by methods such as distillation. In one example, in a first distillation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation product mixture and/or a hydrogenation step as disclosed in, for example, International Patent Application WO 2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower stream comprising primarily phenol, and some cyclohexanone. Cyclohexanone cannot be completely separated from phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., co-assigned, co-pending International Patent Applications WO 2013/165656A1 and WO 2013/165659, the contents of which are incorporated herein by reference in their entirety. An upper fraction comprising cyclohexanone and a lower fraction comprising phenol and the extractive solvent can be obtained. In a subsequent distillation column, the lower fraction can then be separated to obtain an upper fraction comprising a phenol product and a lower fraction comprising the extractive solvent.

Separation and Hydrogenation

At least a portion, preferably the whole, of the neutralized cleavage effluent (cleavage reaction product) may be separated and a phenol-containing fraction thereof can be hydrogenated to covert a portion of the phenol to cyclohexanone in accordance with the present invention. Examples of the separation and hydrogenation process and/or system are illustrated in the attached drawings and described in detail below.

It should be understood that process and/systems shown in the schematic, not-to-scale drawings are only for the purpose of illustrating the general material and/or heat flows and general operating principles. To simplify illustration and description, some routine components, such as pumps, valves, reboilers, pressure regulators, heat exchangers, recycling loops, condensers, separation drums, sensors, rectifiers, fillers, distributors, stirrers, motors, and the like, are not shown in the drawings or described herein. One having ordinary skill in the art, in light of the teachings herein, can add those components where appropriate.

FIGS. 1, 2, 3, 4, 5, 6, and 9 illustrate processes and systems that do not include an anterior or posterior stripper distillation column before or after the primary fractionation column for separating cyclohexanone from phenol for the purpose of poison removal from the hydrogenation feed. Nonetheless, because these drawings show systems and processes on which the present invention is based, they are included and described herein.

FIG. 1 is a schematic diagram showing a process/system 101 for making cyclohexanone from a mixture comprising phenol, cyclohexanone and cyclohexylbenzene including a primary fractionation column T1 (i.e., the first distillation column), a hydrogenation reactor R1, and a cyclohexanone purification column T2 (i.e., the second distillation column). Feed 103 from storage S1, comprising phenol, cyclohexanone, and cyclohexylbenzene, is fed into the primary fractionation column T1.

Feed 103 can be produced by any method. A preferred method is by cleaving a cyclohexylbenzene hydroperoxide in the presence of an acid catalyst such as $H_2SO_4$ and cyclohexylbenzene as described above. Feed 103 may further comprise impurities other than cyclohexylbenzene such as: hydrogenation catalyst poisons; light components (defined above) such as water, methylcyclopentanone, pentanal, hexanal, benzoic acid, and the like, and heavy components such as methylcyclopentylbenzene, bicyclohexane, sulfate of an organic amine (such as 1,6-hexamethylenediame, 2-methyl-1,5-pentamethylenediamine, ethylenediamine, propylenediamine, diethylenetriamine, and the like) produced by injecting the amine into the cleavage mixture to neutralize the liquid acid catalyst used. Feed 103 may further comprise olefins heavier than cyclohexanone such as phenylcyclohexene isomers, hydroxylcyclohexanone, cyclohexenone, and the like. The cyclohexylbenzene hydroperoxide may be produced by aerobic oxidation of cyclohexylbenzene in the presence of a catalyst such as NHPI as described above. The cyclohexylbenzene may be produced by hydroalkylation of benzene in the presence of a hydrogenation/alkylation bi-functional catalyst as described above.

Thus, feed 103 (the first mixture) may comprise, based on the total weight thereof:

cyclohexanone at a concentration of Cxnone(FM1) in a range from x11 wt % to x12 wt %, where x11 and x12 can be, independently: 10, 15, 20, 25, 30, 35, 40, 45, 50, 55, 60, 65, 70, 75, 80, 82, 84, 85, 86, 88, or 90, as long as x11<x12; preferably, 20 wt %≤Cxnone(FM1)≤30 wt %;

phenol at a concentration of Cphol(FM1) in a range from x21 wt % to x22 wt %, where x21 and x22 can be, independently: 10, 15, 20, 25, 30, 35, 40, 45, 50, 55, 60, 65, 70, 75, 80, 82, 84, 85, 86, 88, or 90, as long as x21<x22; preferably, 20 wt %≤Cphol(FM1)≤30 wt %; preferably, 0.3≤Cxnone(FM1)/Cphol(FM1)≤2.0; more preferably 0.5≤Cxnone(FM1)/Cphol(FM1)≤1.5; even more preferably 0.8≤Cxnone(FM1)/Cphol(FM1)≤1.2;

cyclohexylbenzene at a concentration of Cchb(FM1) in a range from x31 wt % to x32 wt %, where x31 and x32 can be, independently: 0.001, 0.005, 0.01, 0.05, 0.1, 0.5, 1, 2, 3, 4, 5, 6, 7, 8, 9, 10, 12, 14, 15, 16, 18, 20, 22, 24, 25, 26, 28, 30, 32, 34, 35, 36, 38, 40, 42, 44, 45, 46, 48, 50, 52, 54, 55, 56, 58, 60, 62, 64, 65, 66, 68, 70, 72, 74, 75, 76, 77, 78, 79, or 80, as long as x31<x32; preferably 30 wt %≤Cchb(FM1)≤60 wt %;

bicyclohexane at a concentration of Cbch(FM1) in a range from x41 wt % to x42 wt %, where x41 and x42 can be, independently: 0, 0.00001, 0.0001, 0.0005, 0.001, 0.005, 0.01, 0.05, 0.1, 0.5, 1, 2, 3, 4, 5, 6, 7, 8, 9, 10, 12, 14, 15, 16, 18, 20, 22, 24, 25, 26, 28, or 30, as long as x41<x42; preferably, 0.001 wt %≤Cbch(FM1)≤1 wt %; and catalyst poison components (e.g., benzoic acid, and other carboxylic acids comprising 1, 2, 3, 4, 5, 6, 7, or 8 carbon atoms, S-containing compounds, and N-containing compounds) at a concentration each of Clc (FM1) in a range from x51 ppm to x52 ppm, where x51 and x52 can be, independently, 0, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000, as long as x51<x52, preferably 1 ppm≤Clc(FM1)≤5000.

From the primary fractionation column T1, a first upper effluent 105 comprising a portion of the cyclohexanone and a portion of light components such as water, methylcyclopentanone, and the like, is produced in the vicinity of the top of the column T1. Effluent 105 may comprise, based on the total weight thereof:

cyclohexanone at a concentration of Cxnone(UE1), where z11 wt %≤Cxnone(UE1)≤z12 wt %, z11 and z12 can be, independently: 60, 65, 70, 75, 80, 85, 90, 91, 92, 93, 94, 95, 96, 97, 98, 99, 99.5, or 99.9, as long as z11<z12; preferably 75≤Cxnone(UE1)≤95;

phenol at a concentration of Cphol(UE1), where z21≤Cphol(UE1)≤z22, z21 and z22 can be, independently: 0, 0.00001, 0.00005, 0.0001, 0.0005, 0.001, 0.005, 0.01, 0.05, 0.1, 0.5, or 1, as long as z21<z22;

cyclohexylbenzene at a concentration of Cchb(UE1), where y31 wt %≤Cchb(UE1)≤y32 wt %, where y31 and y32 can be, independently: 0, 0.00001, 0.00005, 0.0001, 0.0005, 0.001, 0.005, 0.01, 0.05, 0.1, 0.5, or 1, as long as y31<y32;

bicyclohexane at a concentration of Cbch(UE1), where y41 wt %≤Cbch(UE1)≤y42 wt %, y41 and y42 can be, independently: 0, 0.00001, 0.00005, 0.0001, 0.0005, 0.001, 0.005, 0.01, 0.05, 0.1, 0.5, or 1, as long as y41<y42;

cyclohexanol at a concentration of Cxnol(UE1), where z51 wt %≤Cxnol(UE1)≤z52 wt %, based on the total weight of the first upper effluent, where z51 and z52 can be, independently: 0.001, 0.005, 0.01, 0.05, 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10, as long as z51<z52; preferably 0.1 wt %≤Cxnol(UE1)≤5.0 wt %; and catalyst poison components at a total concentration of Clc(UE1), where a61 wt %≤Clc(UE1)≤a62 wt %, where a61 and a62 can be, independently: 0.001, 0.005, 0.01, 0.05, 0.1, 0.5, 1.0, 1.5, 2.0, 2.5, 3.0, 3.5, 4.0, 4.5, or 5.0, as long as a61<a62; preferably 0.001 wt %≤Clc(UE1)≤1.0 wt %;

The first upper effluent 105 is then sent to a cyclohexanone purification column T2, from which a third upper effluent 121 comprising light components such as water, methylcyclopentanone, and the like, is produced at a location in the vicinity of the top of column T2 and then delivered to storage S5. A second upper effluent 123 comprising essentially pure cyclohexanone is produced and sent to storage S7. In the vicinity of the bottom of column T2, a second lower effluent 125 is produced and delivered to storage S9. The second lower effluent can be, e.g., a KA oil comprising both cyclohexanone and cyclohexanol. Thus, the second upper effluent 123 may comprise, based on the total weight thereof, cyclohexanone at a concentration of Cxnone (UE2), where Cxnone(UE2)≥y11 wt %, y11 can be 95, 95.5, 96, 96.5, 97, 97.5, 98, 98.5, 99, 99.5, 99.8, or 99.9. The second lower effluent 125 may comprise, based on the total weight thereof: cyclohexanol at a concentration of Cxnol (LE2), y51 wt %≤Cxnol(LE2)≤y52 wt %, y51 and y52 can be, independently: 10, 12, 14, 15, 16, 18, 20, 22, 24, 25, 26, 28, 30, 32, 34, 35, 36, 38, 40, 42, 44, 45, 46, 48, 50, 52, 54, 55, 56, 58, 60, 62, 64, 65, 66, 68, 70, 72, 74, 75, 76, 78, or 80, as long as y51<y52; and cyclohexanone at a concentration of Cxnone(LE2), e11 wt %≤Cxnol(LE2)≤e12 wt %, e11 and e12 can be, independently: 10, 12, 14, 15, 16, 18, 20, 22, 24, 25, 26, 28, 30, 32, 34, 35, 36, 38, 40, 42, 44, 45, 46, 48, 50, 52, 54, 55, 56, 58, 60, 62, 64, 65, 66, 68, 70, 72, 74, 75, 76, 78, or 80, as long as e11<e12.

The first middle effluent 107 produced from the primary fractionation column T1 comprises phenol at a concentration higher than in feed 103 and higher than in the first upper effluent 105, cyclohexanone at a concentration lower than in both feed 103 and the first upper effluent 105, cyclohexylbenzene at a concentration desirably lower than in feed 103 and higher than in the first upper effluent 105, and one or more of other impurities such as bicyclohexane and cyclohexenone. Thus, effluent 107 may comprise, based on total weight thereof:

cyclohexanone at a concentration of Cxnone(ME1), where a11 wt %≤Cxnone(ME1)≤a12 wt %, a11 and a12 can be, independently: 1, 2, 4, 5, 6, 8, 10, 12, 14, 15, 16, 18, 20, 22, 24, 25, 26, 28, 30, 35, 40, 45, or 50, as long as a11<a12;

phenol at a concentration of Cphol(ME1), where a21 wt %≤Cphol(ME1)≤a22 wt %, based on the total weight of the first middle effluent, where a21 and a22 can be, independently: 10, 15, 20, 25, 30, 35, 40, 45, 50, 55, 60, 65, 70, 75, 80, as long as a21<a22; preferably, 1.0≤Cphol(ME1)/Cxnone(ME1)≤3.0; more preferably, 2.0≤Cphol(ME1)/Cxnone(ME1)≤3.0, close to the ratio in a phenol/cyclohexanone azeotrope;

cyclohexylbenzene at a concentration of Cchb(ME1), where a31 wt %≤Cchb(ME1)≤a32 wt %, a31 and a32 can be, independently: 0.001, 0.005, 0.01, 0.05, 0.1, 0.2, 0.4, 0.5, 0.6, 0.8, 1, 2, 4, 5, 6, 8, 10, 12, 14, 15, 16, 18, 20, 22, 24, 25, 26, 28, or 30, as long as a31<a32;

bicyclohexane at a concentration of Cbch(ME1), where a41 wt %≤Cbch(ME1)≤a42 wt %, a41 and a42 can be, independently: 0.001, 0.005, 0.01, 0.05, 0.1, 0.2, 0.4, 0.5, 0.6, 0.8, 1, 2, 4, 5, 6, 8, 10, 12, 14, 15, 16, 18, 20, 22, 24, 25, 26, 28, or 30, as long as a41<a42;

cyclohexanol at a concentration of Cxnol(ME1), where a51 wt %≤Cbch(ME1)≤a52 wt %, a51 and a52 can be, independently: 0.01, 0.02, 0.04, 0.05, 0.06, 0.08, 0.1, 0.2, 0.4, 0.5, 0.6, 0.8, 1, 2, 4, 5, 6, 8, 10, 12, 14, 15, 16, 18, 20, 22, 24, 25, 26, 28, or 30, as long as a51<a52; preferably 0.01 wt %≤Cxnol(ME1)≤5 wt %; and catalyst poison components (e.g., benzoic acid, and other organic acid comprising 1, 2, 3, 4, 5, 6, 7, or 8 carbon atoms, S-containing compounds, and N-containing compounds) each at a concentration of Clc(ME1), where a71 ppm≤Clc(UE1)≤a72 ppm, where a71 and a72 can be, independently: 0, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, as long as a71<a72, preferably 1 ppm≤Clc(FM1)≤1000.

Preferably, effluent 107 is essentially free of catalyst poison components that may poison the hydrogenation catalyst used in the hydrogenation reactor(s). However, depending on the quality of feed 103, effluent 107 may comprise catalyst poison components at concentrations capable of leading to poisoning of the hydrogenation catalyst, as discussed above. In such case, the present invention (exemplified and illustrated in FIGS. 7 and 8 and described in detail below) may be advantageously used to reduce the catalyst poison components from effluent 107 before it is fed into the hydrogenation reactor as the whole or a portion of the hydrogenation feed.

Effluent 107, if containing catalyst poison components capable of poisoning the hydrogenation catalyst at acceptable concentration(s), can be directly delivered to a hydrogenation reactor R1, where it is mixed with a hydrogen gas feed 112 comprising fresh make-up hydrogen stream 111 from storage S3 and recycle hydrogen 117. The phenol contained in feed 107 and hydrogen reacts with each other in the presence of a catalyst bed 113 inside reactor R1 to produce cyclohexanone. Some of the cyclohexanone inside the reactor R1 reacts with hydrogen in the presence of the catalyst bed 113 as well to produce cyclohexanol. In the exemplary process shown in FIG. 1, surplus hydrogen is fed into reactor R1. It is contemplated that a second phenol-containing stream (not shown), separate from and independent of effluent 107, may be fed into the hydrogenation reactor R1. Such additional feed can advantageously contain phenol at a concentration of Cphol(FP), d21 wt %≤Cphol (FP)≤d22 wt %, based on the total weight of the second phenol-containing stream, where d21 and d22 can be, independently: 50, 55, 60, 65, 70, 75, 80, 85, 90, 91, 92, 93, 94, 95, 96, 97, 98, 99, or 100, as long as d21<d22. Preferably, the second phenol-containing stream comprises substantially pure phenol produced by any process, such as the conventional cumene process, coal-based processes, and the like.

The total hydrogenation feed, including stream 107 and optional additional streams, delivered to the hydrogenation reactor R1, if blended together before being fed into R1, may have an overall composition containing phenol at a concentration of Cphol(A), cyclohexanone at a concentration of Cxnone(A), cyclohexylbenzene at a concentration of Cchb(A), and bicyclohexane at a concentration of Cbch(A), wherein the concentrations are in the following ranges, based on the total weight of the hydrogenation feed:

a1 wt %≤Cxnone(A)≤a2 wt %, where a1 and a2 can be, independently: 0.1, 0.2, 0.3, 0.4, 0.5, 0.6, 0.7, 0.8, 0.9, 1, 2, 4, 5, 6, 8, 10, 12, 14, 15, 16, 18, 20, 22, 24, 25, 26, 28, 30, 32, 34, 35, 36, 38, 40, 42, 44, 45, 46, 48, 50, as long as a1<a2;

b1 wt %≤Cphol(A)≤b2 wt %, where b1 and b2 can be, independently: 10, 15, 20, 25, 30, 35, 40, 45, 50, 55, 60, 65, 70, 75, 80, 82, 84, 85, 86, 88, 90, 91, 92, 93, 94, 95, 96, 97, 98, or 99, as long as a21<a22;

c1 wt %≤Cchb(A)≤c2 wt %, where c1 and c2 can be, independently: 0.001, 0.005, 0.01, 0.05, 0.1, 0.2, 0.4, 0.5, 0.6, 0.8, 1, 2, 4, 5, 6, 8, 10, 12, 14, 15, 16, 18, 20, 22, 24, 25, 26, 28, or 30, as long as c1<c2; preferably, 1 wt %≤Cchb(A)≤20 wt %; and d1 wt %≤Cbch(A)≤d2 wt %, where d1 and d2 can be, independently: 0.001, 0.005, 0.01, 0.05, 0.1, 0.2, 0.4, 0.5, 0.6, 0.8, 1, 2, 4, 5, 6, 8, 10, 12, 14, 15, 16, 18, 20, 22, 24, 25, 26, 28, or 30, as long as d1<d2; preferably, 1 wt %≤Cbch(A)≤20 wt %.

In the hydrogenation reaction zone, the following reactions can take place, resulting in an increase of concentrations of cyclohexanone, cyclohexanol, and bicyclohexane, and a decrease of concentrations of phenol, cyclohexanone, and cyclohexylbenzene:

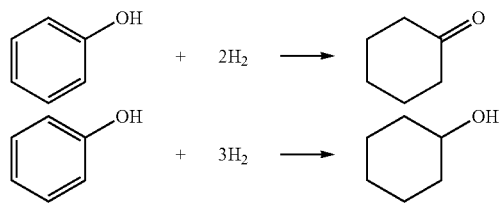

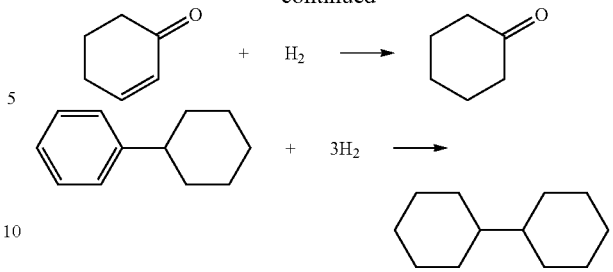

Cyclohexanone may hydrogenate to make cyclohexanol in the hydrogenation reactor R1. Because the net effect of the reaction is an overall increase of cyclohexanone concentration, this reaction is not included in the above paragraph. Nonetheless, cyclohexanone can engage in competition against phenol for hydrogen, which should be reduced or inhibited.

The total amount of hydrogen, including fresh, make-up hydrogen and recycled hydrogen, fed into the reactor R1, and the total amount of phenol fed into the hydrogenation reaction zone desirably exhibit a hydrogen to phenol molar ratio of R(H2/phol), where R1≤R(H2/phol)≤R2, R1 and R2 can be, independently: 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10, as long R1<R2. While a higher R(H2/phol) ratio can result in higher overall conversion of phenol, it tends to result in higher conversion of cyclohexanone, higher selectivity of phenol to cyclohexanol, and higher conversion of cyclohexylbenzene, as well. Therefore, it is generally desirable that in the hydrogenation reactor R1, the reaction conditions, including but not limited to temperature, pressure, and R(H2/phol) ratio, and catalysts, are chosen such that the overall conversion of phenol is not too high.

The hydrogenation reactions take place in the presence of a hydrogenation catalyst. The hydrogenation catalyst may comprise a hydrogenation metal performing a hydrogenation function supported on a support material. The hydrogenation metal can be, e.g., Fe, Co, Ni, Ru, Rh, Pd, Ag, Re, Os, Ir, and Pt, and mixtures and combinations of one or more thereof. The support material can be advantageously an inorganic material, such as oxides, glasses, ceramics, molecular sieves, and the like. For example, the support material can be activated carbon, $Al_2O_3$, $Ga_2O_3$, $SiO_2$, $GeO_2$, SnO, $SnO_2$, $TiO_2$, $ZrO_2$, $Sc_2O_3$, $Y_2O_3$, alkali metal oxides, alkaline earth metal oxides, and mixtures, combinations, complexes, and compounds thereof. The concentration of the hydrogenation metal can be, e.g., in a range from Cm1 wt % to Cm2 wt %, based on the total weight of the catalyst, where Cm1 and Cm2 can be, independently: 0.001, 0.005, 0.01, 0.05, 0.1, 0.5, 1.0, 1.5, 2.0, 2.5, 3.0, 3.5, 4.0, 4.5, 5.0, as long as Cm1<Cm2.

Without intending to be bound by any particular theory, it is believed that the above hydrogenation reactions occur quickly in the presence of the hydrogenation metal. Therefore, it is highly desirable that the hydrogenation metal is preferentially distributed in the outer rim of the catalyst particles, i.e., the concentration of the hydrogenation metal in the catalyst particle surface layer is higher than in the core thereof. Such rimmed catalyst can reduce the overall hydrogenation metal loading, reducing cost thereof, especially if the hydrogenation metal comprises a precious metal such as Pt, Pd, Ir, Rh, and the like. The low concentration of hydrogenation metal in the core of the catalyst particle also leads to lower chance of hydrogenation of cyclohexanone, which may diffuse from the surface to the core of the catalyst particles, resulting in higher selectivity of cyclohexanone in the overall process.

As discussed above, certain light components, such as organic acids (e.g., formic acid, acetic acid, propanoic acid, linear, linear branched and cyclic carboxylic acids comprising 5, 6, 7, or 8 carbon atoms such as benzoic acid), N-containing compounds (e.g., amines, imides, amides, $NO_2$-substituted organic compounds), S-containing compounds (sulfides, sulfites, sulfates, sulfones), if contained in the reaction mixture in the hydrogenation reactor and allowed to contact the hydrogenation metal under the hydrogenation reaction conditions, poisoning of the hydrogenation catalyst can occur, leading to reduction of performance or premature failure of the catalyst. To avoid catalyst poisoning, it is highly desirable that the hydrogenation feed comprises such catalyst poison components at low concentrations described above.

It is believed that the catalyst surface can have different degrees of adsorption affinity to the different components in the reaction media such as phenol, cyclohexanone, cyclohexanol, cyclohexenone, cyclohexylbenzene, and bicyclohexane. It is highly desired that the catalyst surface has higher adsorption affinity to phenol than to cyclohexanone and cyclohexylbenzene. Such higher phenol adsorption affinity will give phenol competitive advantages in the reactions, resulting in higher selectivity to cyclohexanone, lower selectivity of cyclohexanol, and lower conversion of cyclohexylbenzene, which are all desired in a process designed for making cyclohexanone. In addition, in order to favor the conversion of phenol to cyclohexanone over the conversion of cyclohexylbenzene to bicyclohexane and the conversion of cyclohexanone to cyclohexanol, it is highly desired that the phenol concentration in the reaction medium in the hydrogenation reactor R1 is relatively high, so that phenol molecules occupy most of the active catalyst surface area. Therefore, it is desired that the overall conversion of phenol in the reactor R1 is relatively low.

As such, it is desired that in the hydrogenation reactor R1, the selectivity of phenol to cyclohexanone is Sel(phol)a, the selectivity of phenol to cyclohexanol is Sel(phol)b, and at least one of the following conditions (i), (ii), (iii), and (iv) is met:

$$30\% \leq Con(phol) \leq 95\%; \qquad (i)$$

$$0.1\% \leq Con(chb) \leq 20\%; \qquad (ii)$$

$$80\% \leq Sel(phol)a \leq 99.9\%; \text{ and} \qquad (iii)$$

$$0.1\% \leq Sel(phol)b \leq 20\%. \qquad (iv)$$

The feed(s) to the hydrogenation reactor R1 may further comprise cyclohexenone at a concentration of Cxenone(A), where e1 wt % ≤ Cxenone(A) ≤ e2 wt %, based on the total weight of the hydrogenation feed, e1 and e2 can be, independently: 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3.5, 4, 4.5, or 5, as long as e1<e2. It is highly desired that in step (B), the conversion of cyclohexenone is Con(xenone), Con5% ≤ Con(xenone) ≤ Con6%, where Con5 and Con6 can be, independently: 85, 86, 87, 88, 89, 90, 91, 92, 93, 94, 95, 96, 97, 98, 99, 100, as long as Con5<Con6. Thus, a great majority of the cyclohexenone contained in the feed(s) is converted into cyclohexanone in the hydrogenation reactor R1.

At the bottom of reactor R1, a hydrogenation reaction product stream 115 comprising phenol at a concentration lower than in stream 107, cyclohexanone at a concentration higher than in stream 107, cyclohexylbenzene, bicyclohexane, and surplus hydrogen is taken. Stream 115 may comprise, based on the total weight thereof:

Cyclohexanone at a concentration of Cxnone(HRP), where b11 wt % ≤ Cxnone(HRP) ≤ b12 wt %, b11 and b12 can be, independently: 20, 25, 30, 35, 40, 45, 50, 55, 60, 65, 70, 75, 80, 85, 90, as long as b11<b12;

Phenol at a concentration of Cphol(HRP), where b21 wt % ≤ Cphol(HRP) ≤ b22 wt %, b21 and b22 can be, independently: 1, 2, 5, 6, 8, 10, 12, 14, 15, 16, 18, 20, 22, 24, 25, 26, 28, 30, 40, 50, as long as b21<b22;

cyclohexylbenzene at a concentration of Cchb(HRP), where b31 wt % ≤ Cchb(HRP) ≤ b32 wt %, b31 and b32 can be, independently: 0.001, 0.005, 0.01, 0.05, 0.1, 0.2, 0.4, 0.5, 0.6, 0.8, 1, 2, 4, 5, 6, 8, 10, 12, 14, 15, 16, 18, 20, 22, 24, 25, 26, 28, 30, as long as b31<b32;

bicyclohexane at a concentration of Cbch(HRP), where b41 wt % ≤ Cbch(HRP) ≤ b42 wt %, b41 and b42 can be, independently: 0.001, 0.005, 0.01, 0.05, 0.1, 0.2, 0.4, 0.5, 0.6, 0.8, 1, 2, 4, 5, 6, 8, 10, 12, 14, 15, 16, 18, 20, 22, 24, 25, 26, 28, 30, as long as b41<b42; and cyclohexanol at a concentration of Cxnol(HRP), where b51 wt % ≤ Cxnol(HRP) ≤ b52 wt %, b51 and b52 can be, independently: 0.01, 0.02, 0.04, 0.05, 0.06, 0.08, 0.1, 0.2, 0.4, 0.5, 0.6, 0.8, 1, 2, 4, 5, 6, 8, 10, as long as b51<b52.

Preferably, at least one of the following criteria is met in the hydrogenation reaction product stream 115:

Ra31 ≤ Cchb(ME1)/Cchb(HRP) ≤ Ra32, where Ra31 and Ra32 can be, independently: 0.10, 0.20, 0.30, 0.40, 0.50, 0.60, 0.70, 0.75, 0.80, 0.85, 0.90, 0.92, 0.94, 0.95, 0.96, 0.98, 1.00, 1.02, 1.04, 1.05, 1.06, 1.08, 1.10, 1.15, 1.20, 1.25, 1.30, 1.35, 1.40, 1.50, 1.60, 1.70, 1.80, 1.90, 2.00, 3.00, 4.00, 5.00, 6.00, 7.00, 8.00, 9.00, or 10.0, as long as Ra31<Ra32; more preferably, 0.80 ≤ Cchb(ME1)/Cchb(HRP) ≤ 1.00, meaning that cyclohexylbenzene concentration does not decrease significantly in the hydrogenation reaction zone;

Ra41 ≤ Cbch(HRP)/Cbch(ME1) ≤ Ra42, where Ra41 and Ra42 can be, independently: 0.10, 0.20, 0.30, 0.40, 0.50, 0.60, 0.70, 0.75, 0.80, 0.85, 0.90, 0.92, 0.94, 0.95, 0.96, 0.98, 1.00, 1.02, 1.04, 1.05, 1.06, 1.08, 1.10, 1.15, 1.20, 1.25, 1.30, 1.35, 1.40, 1.50, 1.60, 1.70, 1.80, 1.90, 2.00, 3.00, 4.00, 5.00, 6.00, 7.00, 8.00, 9.00, or 10.0, as long as Ra41<Ra42; preferably, 1.0 ≤ Cbch(HRP)/Cbch(ME1) ≤ 1.5, meaning that bicyclohexane concentration does not increase significantly in the hydrogenation reaction zone; and Ra51 ≤ Cxnol(HRP)/Cxnol(ME1) < Ra52, where Ra51 and Ra52 can be, independently: 0.10, 0.20, 0.30, 0.40, 0.50, 0.60, 0.70, 0.75, 0.80, 0.85, 0.90, 0.92, 0.94, 0.95, 0.96, 0.98, 1.00, 1.02, 1.04, 1.05, 1.06, 1.08, 1.10, 1.15, 1.20, 1.25, 1.30, 1.35, 1.40, 1.50, 1.60, 1.70, 1.80, 1.90, 2.00, 3.00, 4.00, 5.00, 6.00, 7.00, 8.00, 9.00, or 10.0, as long as Ra51<Ra52; preferably, 1.0 ≤ Cxnol(HRP)/Cxnol(ME1) ≤ 1.5, meaning that cyclohexanol concentration does not increase significantly in the hydrogenation reaction zone.

Stream 115 is then delivered to a separation drum D1, where a vapor phase comprising a majority of the surplus hydrogen and a liquid phase is obtained. The vapor phase can be recycled as stream 117 to reactor R1 as part of the hydrogen supply, and the liquid phase 119 is recycled to the primary fractionation column T1 at one or more side locations on column T1, at least one of which is above the location where the first middle effluent 107 is taken, but below the location where the first upper effluent 105 is taken.

The first bottom effluent 109 obtained from the primary fractionation column T1 comprises primarily heavy components such as cyclohexylbenzene, bicyclohexane, amine salts mentioned above, C18+, C12 oxygenates, and C18+ oxygenates. This fraction is delivered to a heavies distillation column T3 (the third distillation column), from which a fourth upper effluent 127 desirably comprising cyclohexylbenzene at a concentration higher than C31 wt % and a lower effluent 129 are produced, where C31 can be 80, 82, 84, 85, 86, 88, 90, 92, 94, 95, 96, 98, or 99. Effluent 127 may be delivered to storage S11 and effluent 129 to storage S13. Effluent 127 may further comprise olefins, primarily phenylcyclohexene isomers, at a non-negligible amount. It may be desirable to subject effluent 127 to hydrogenation to reduce olefin concentrations, and subsequently recycle the hydrogenated effluent 127 to an earlier step such as cyclohexylbenzene oxidation to convert at least a portion of it to cyclohexylbenzene hydroperoxide, such that the overall yield of the process is improved.

Figure 2:
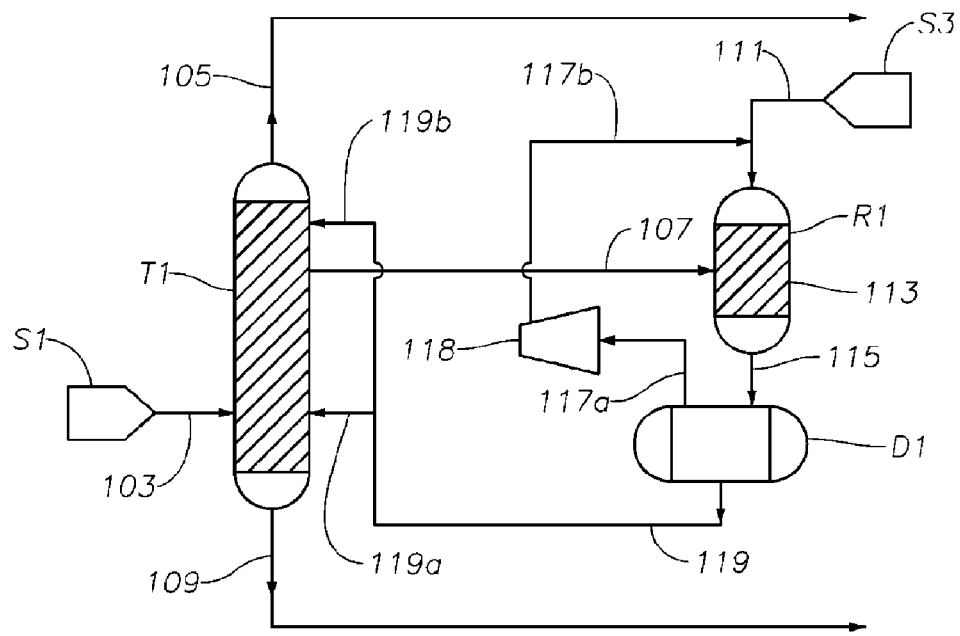
FIG. 2 is a schematic diagram showing a portion of a process/system similar to the process/system shown in FIG. 1, but comprising modified fluid communications between and/or within the primary fractionation column T1 and the hydrogenation reactor R1.

FIG. 2 is a schematic diagram showing a portion of a process/system similar to the process/system shown in FIG. 1, but comprising modified fluid communications between and/or within the primary fractionation column T1 and the hydrogenation reactor R1. In this figure, the hydrogenation reaction product 115 comprises residual hydrogen, as in the example shown in FIG. 1. Effluent 115 is first delivered into separation drum D1, where a hydrogen-rich vapor stream 117a is obtained, compressed by a compressor 118, and then delivered to reactor R1 as a stream 117b together with fresh, make-up hydrogen stream 111 into reactor R1. A liquid stream 119 is obtained from separation drum D1, then divided into multiple streams (two recycle streams 119a and 119b shown in FIG. 2), recycled to two different locations on the side of column T1, one below the location where the first middle effluent 107 is taken (shown at approximately the same level as feed 103), and the other above the location where the first middle effluent 107 is drawn. This modified recycle fluid communication between the hydrogenation reactor R1 and the primary fractionation column T1 compared to FIG. 1 has surprising advantages. It was found that where the recycle liquid stream 119 is fed to one location only, such as at a location above the first middle effluent 107, bicyclohexane is continuously produced in reactor R1 from the cyclohexylbenzene in stream 107, and then steadily accumulates in column T1 to such high concentration that a separate phase can form, interfering with effective product separation in column T1. On the other hand, where the recycle stream 119 is recycled back to column T1 at multiple locations on T1 (as shown in FIG. 2), the probability of forming a separate bicyclohexane phase inside T1 is drastically reduced or eliminated.

Figure 3:
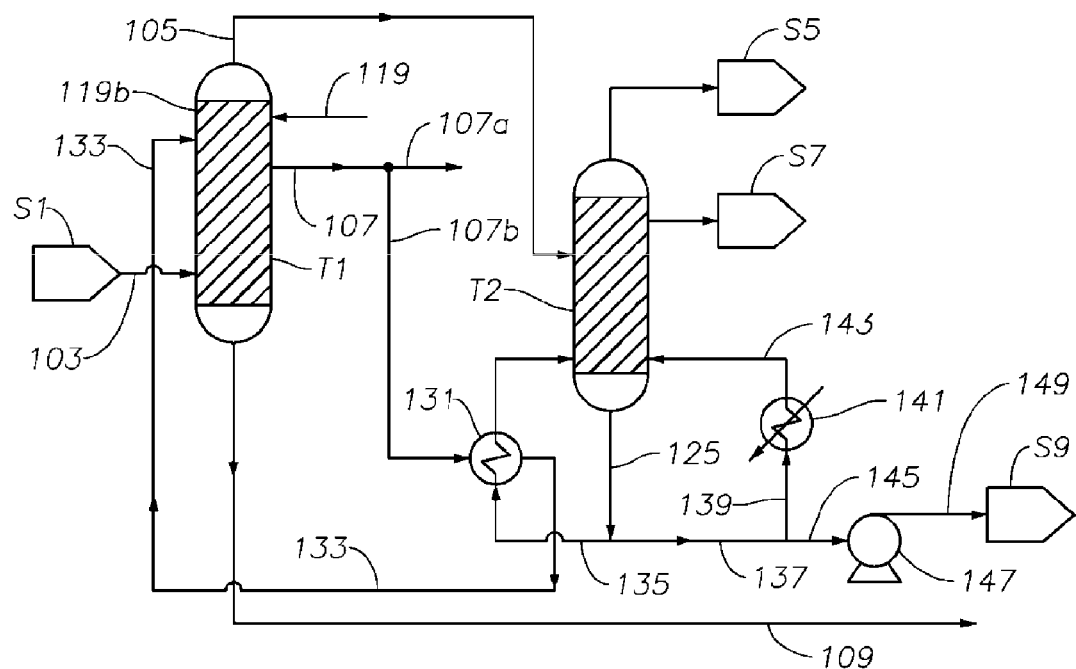
FIG. 3 is a schematic diagram showing a portion of a process/system similar to those shown in FIGS. 1 and 2, but comprising modified fluid communications and/or heat transfer arrangement between and/or within the primary fractionation column T1 and the cyclohexanone purification column T2.

FIG. 3 is a schematic diagram showing a portion of a process/system similar to those shown in FIGS. 1 and 2 comprising modified fluid communications and/or heat transfer arrangement between and/or within the primary fractionation column T1 and the cyclohexanone purification column T2. In this figure, the hydrogenation reactor R1 and its peripheral equipment are not shown. In this figure, the first middle effluent 107 drawn from column T1 is divided into multiple streams (two streams 107a and 107b shown), one of which (107a) is delivered to the hydrogenation reactor R1 (not shown) as hydrogenation feed, and the other (107b) to a heat exchanger 131 in fluid and thermal communication with the cyclohexanone purification column T2. In this figure, the bottom stream 125 (e.g., comprising a mixture of cyclohexanone and cyclohexanol) from column T2 is divided into three streams: stream 135 which passes through heat exchanger 131 and is heated by stream 107b; stream 139 which is heated by a heat exchanger 141 and then recycled to column T2; and stream 145, which is delivered to storage S9 via pump 147. Stream 107b becomes a cooler stream 133 after passing through heat exchanger 131, and is then subsequently recycled to primary fractionation column T1 at one or more locations, at least one of which is located above the location where the first middle effluent 107 is drawn. A heat management scheme as illustrated in FIG. 3 can significantly improve the energy efficiency of the overall process and system.

Figure 4:
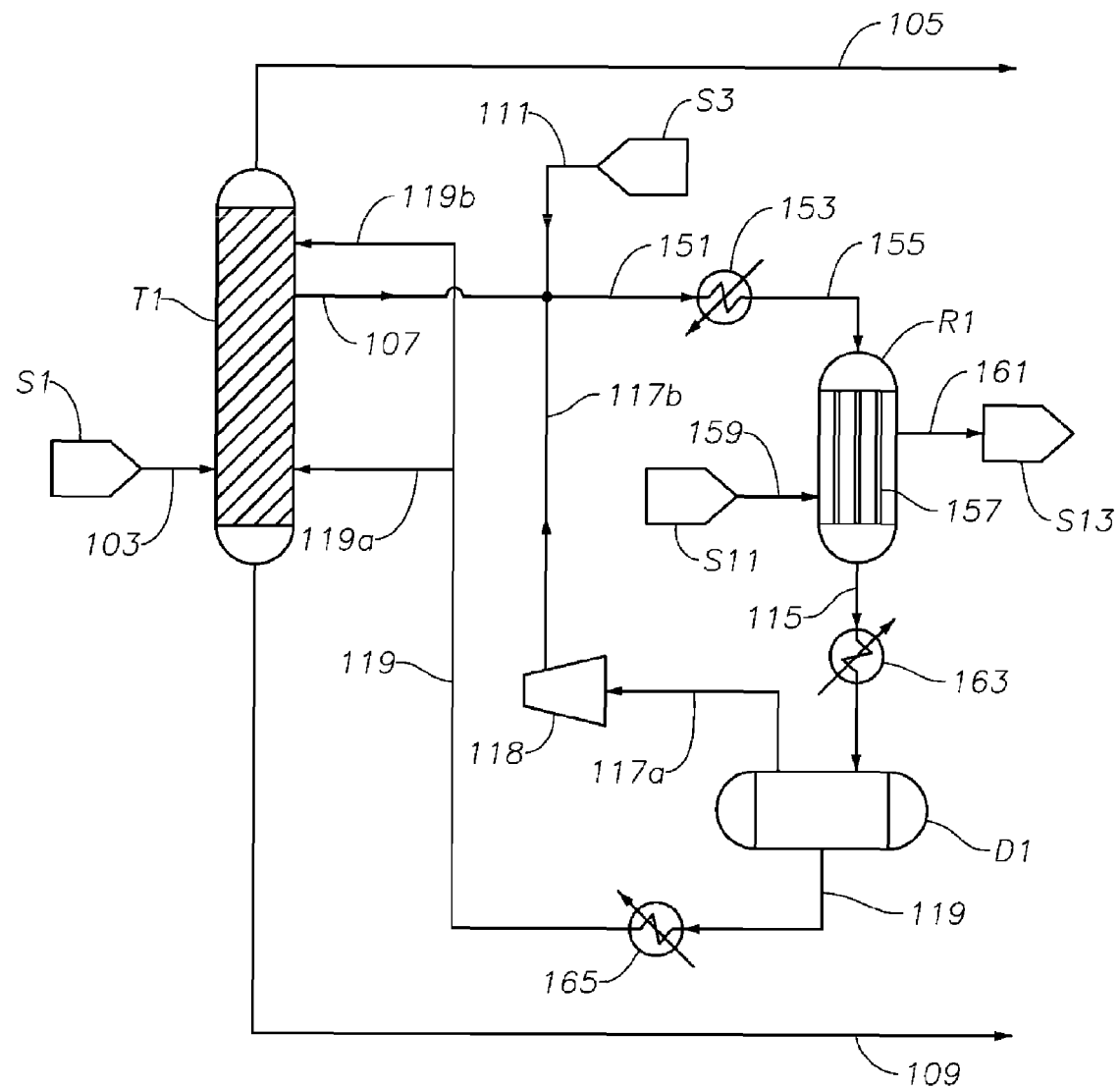
FIG. 4 is a schematic diagram showing a portion of a process/system similar to those shown in FIGS. 1 to 3, but comprising a tubular heat exchanger-type hydrogenation reactor R1, where the hydrogenation reaction occurs primarily in vapor phase.

FIG. 4 is a schematic diagram showing a portion of a process/system similar to those shown in FIGS. 1-3, but comprising a tubular heat exchanger-type hydrogenation reactor. This figure illustrates an example where the hydrogenation reactor R1 operates under hydrogenation conditions such that a majority of the phenol and/or cyclohexylbenzene present in the reaction media inside the reactor R1 are in vapor phase. In this figure, the first middle effluent 107 taken from the primary fractionation column T1 is first combined with hydrogen feeds (including fresh make-up hydrogen stream 111 and recycle hydrogen stream 117b), heated by a heat exchanger 153 and then delivered to a tubular heat-exchanger type hydrogenation reaction R1 having hydrogenation catalyst installed inside the tubes 157. A stream of cooling media 159 such as cold water supplied from storage S11 passes through the shell of the exchanger/reactor R1 and exits the reactor R1 as a warm stream 161 and is then delivered to storage S13, thereby a significant amount of heat released from phenol hydrogenation reaction is carried away, maintaining the temperature inside the reactor R1 in a range from $T1°$ C. to $T2°$ C., and an absolute pressure inside the reactor R1 in a range from P1 kPa to P2 kPa, where T1 and T2 can be, independently: 140, 145, 150, 155, 160, 165, 170, 175, 180, 185, 190, 195, 200, 205, 210, 215, 220, 225, 230, 235, 240, 250, 260, 270, 280, 290, 300, as long as T1<T2, and P1 and P2 can be, independently: 100, 110, 120, 130, 140, 150, 160, 170, 180, 190, 200, 250, 300, 350, or 400, as long as P1<P2. Preferably T2=240 and P2=200. Alternatively, the cooling medium may comprise at least a portion of the hydrogenation feed in liquid phase, such that at least a portion of the feed is vaporized, and at least a portion of the vapor feed is then fed to the hydrogenation reactor R1.

Because heat transfer of a vapor phase is not as efficient as a liquid phase, and the phenol hydrogenation reaction is highly exothermic, it is highly desired that heat transfer is carefully managed in such vapor phase hydrogenation reactor. Other types of reactors suitable for a liquid phase reaction can be used as well. For example, fixed-bed reactors configured to have intercooling capability and/or quenching options, so that the heat generated in the reaction can be taken away sufficiently quickly to maintain the reaction media in a desirable temperature range.

Figure 5:
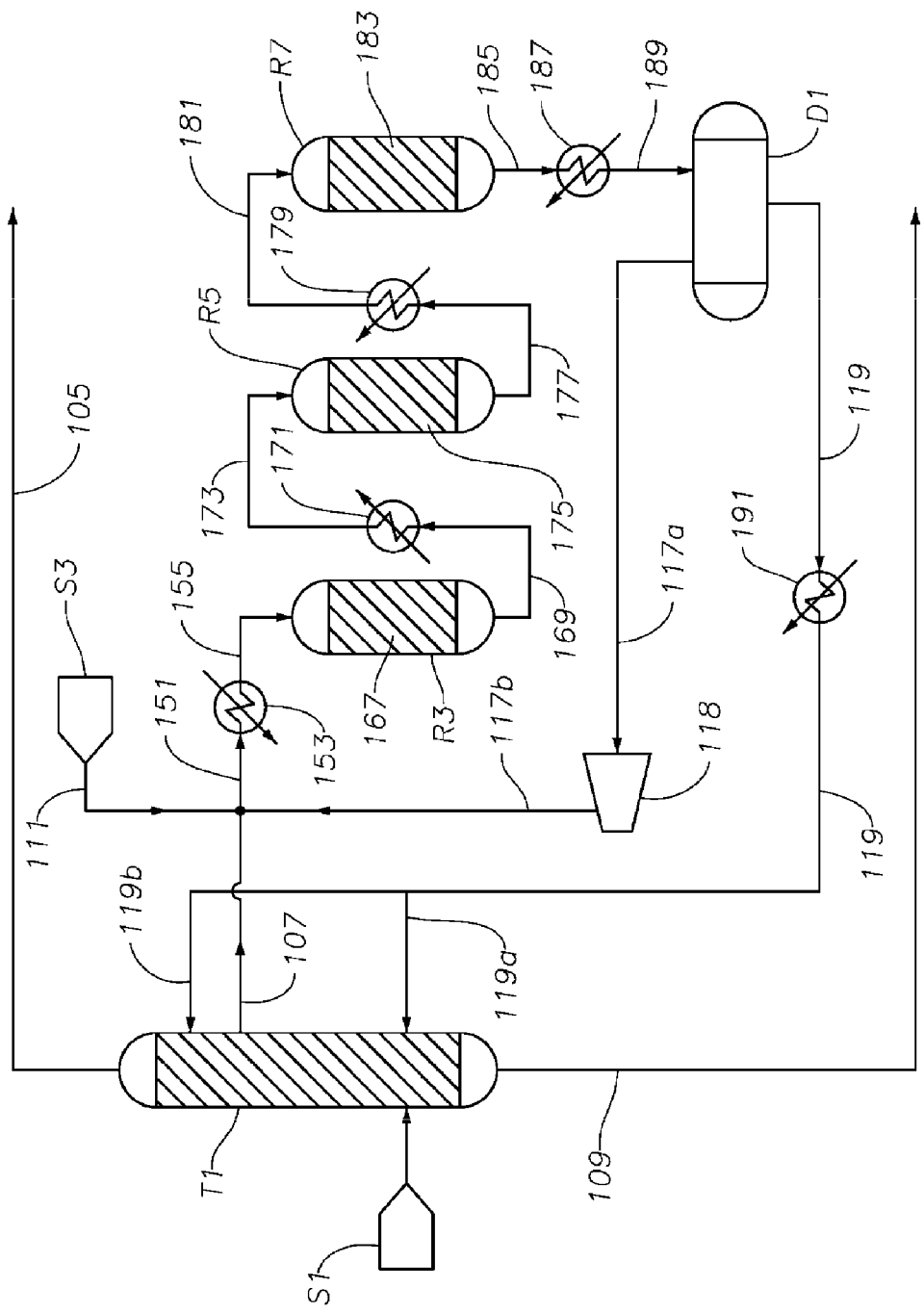
FIG. 5 is a schematic diagram showing a portion of a process/system similar to those shown in FIGS. 1 to 4, but comprising three hydrogenation reactors R3, R5, and R7 connected in series, where the hydrogenation reaction occurs primarily in liquid phase.

FIG. 5 is a schematic diagram showing a portion of a process/system similar to those shown in FIGS. 1-4, but comprising three fixed bed hydrogenation reactors R3, R5, and R7 connected in series. This figure illustrates an example where the hydrogenation reactors operate under hydrogenation conditions such that a majority of the phenol and/or cyclohexylbenzene present in the reaction media inside the reactors R3, R5, and R7 are in liquid phase. In this figure, the first middle effluent 107 taken from the primary fractionation column T1 is first combined with hydrogen feeds (including fresh make-up hydrogen stream 111 and recycle hydrogen stream 117b) to form a feed stream 151, then heated by a heat exchanger 153, and then delivered as stream 155 to a first hydrogenation reactor R3 having a catalyst bed 167 inside. A portion of the phenol is converted to cyclohexanone in reactor R3, releasing a moderate amount of heat raising the temperature of the reaction media. Effluent 169 exiting reactor R3 is then cooled down by heat exchanger 171, and then delivered into a second fixed bed reactor R5 having a catalyst bed 175 inside. A portion of the phenol contained in the reaction media is converted to cyclohexanone in reactor R5, releasing a moderate amount of heat raising the temperature inside the reactor R5. Effluent 177 exiting reactor R5 is then cooled down by heat exchanger 179, and then delivered to a third fixed bed hydrogenation reactor R7 having a catalyst bed 183 inside. A portion of the phenol contained in the reaction media is converted to cyclohexanone in reactor R7, releasing a moderate amount of heat raising the temperature inside the reactor R7. Effluent 185 exiting reactor R7 is then cooled down by heat exchanger 187, and delivered to drum D1, where a vapor phase 117a and a liquid phase 119 are obtained. By using multiple reactors in the hydrogenation reaction zone, and the use of heat exchangers between adjacent reactors and after each reactor, temperatures inside the reactors R3, R5, and R7 are each independently maintained in a range from T3° C. to T4° C., and the absolute pressures inside reactors R3, R5, and R7 are each independently maintained in a range from P3 kPa to P4 kPa, where T3 and T4 can be, independently: 140, 145, 150, 155, 160, 165, 170, 175, 180, 185, 190, 195, 200, 205, 210, 215, 220, 225, 230, 235, 240, 250, 260, 270, 280, 290, 300, as long as T3<T4, and P3 and P4 can be, independently: 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1134, 1150, 1175, 1200, as long as P3<P4. Preferably, T4=240 and P4=1134. In general, higher temperature favors the production of cyclohexanol over cyclohexanone. Thus, it is highly desirable that the hydrogenation is conducted at a temperature no higher than 220° C.

Figure 6:
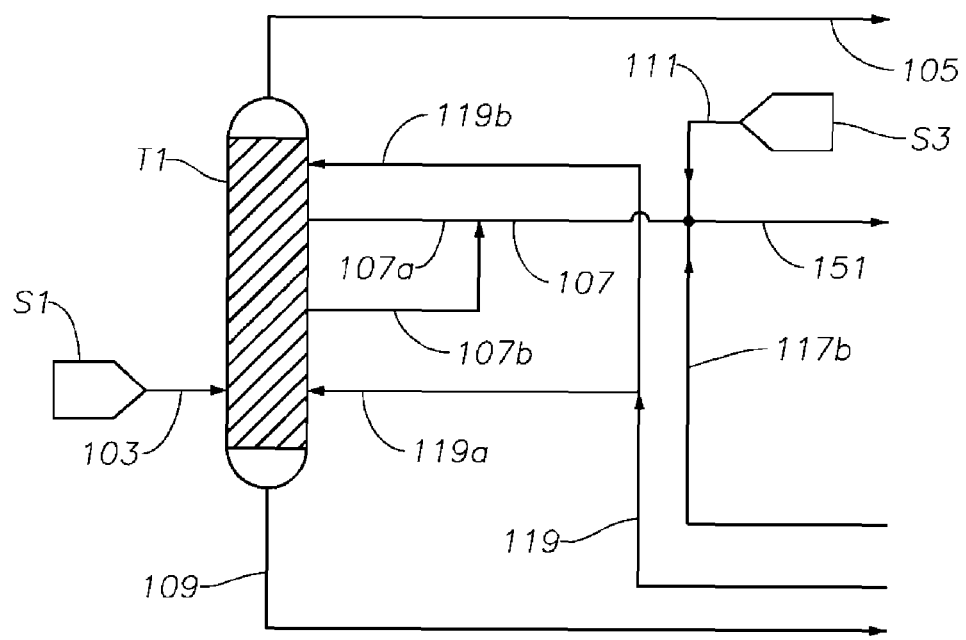
FIG. 6 is a schematic diagram showing a portion of a process/system similar to those shown in FIGS. 1 to 5, but comprising modified fluid communications between and/or within the primary fractionation column T1 and the hydrogenation reactor R1.

FIG. 6 is a schematic diagram showing a portion of a process/system similar to the process/system shown in FIGS. 1-5, but comprising modified fluid communications between and/or within the primary fractionation column T1 and the hydrogenation reactor R1. In this figure, two middle effluents, including a first middle effluent 107a and a second middle effluent 107b, are drawn from the side of the primary fractionation column T1. The two effluents 107a and 107b have differing compositions, and are combined to form a feed 107, which is then combined with hydrogen feed streams 111 and 117b and delivered to the hydrogenation reactor(s). Drawing two middle effluents with different compositions at different locations have unexpected technical advantages. It was found that if only one middle effluent is drawn from a single location on column T1, certain undesirable components, such as hydroxycyclohexanone(s), can accumulate in column T1. It is believed that hydroxycyclohexanone(s) can undergo dehydration to form cyclohexenone, which can cause fouling inside column T1. By drawing middle effluents at different height locations on the column, one can effectively reduce the accumulation of such undesirable components and the probability of fouling inside the column.

Figure 7:
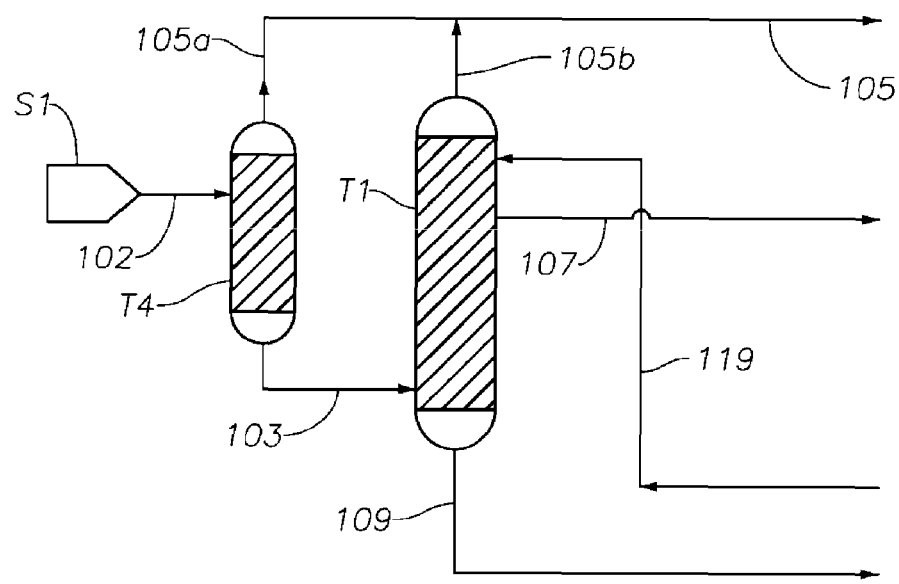
FIG. 7 is a schematic diagram showing a portion of a process/system similar to those shown in FIGS. 1 to 6, but comprising an anterior stripper distillation column T4 before the primary fractionation column T1 configured for removing at least a portion of the catalyst poison components from the phenol/cyclohexanone/cyclohexylbenzene feed fed to the primary fractionation column T1 to reduce or prevent catalyst poisoning in the hydrogenation reactor.

FIG. 7 is a schematic diagram showing a portion of an exemplary process/system of the present disclosure similar to those shown in FIGS. 1-6, but comprising an anterior stripper distillation column T4 before the primary fractionation column T1 configured for removing at least a portion of the catalyst poison components and/or the light components from a crude feed (crude mixture) to reduce or prevent catalyst poisoning in the hydrogenation reactor. A crude mixture feed stream 102 is first fed into T4, which is smaller than column T1, to obtain an upper effluent 105a (upper anterior stripper effluent) rich in light components and depleted with or low in phenol and cyclohexylbenzene and a lower effluent 103 (lower anterior stripper effluent) depleted with or low in the catalyst poison components and/or the light components. The upper effluent 105a is then combined with the first upper effluent 105b obtained from the primary fractionation column T1 to form a stream 105, which is then delivered to the cyclohexanone purification column T2. The lower effluent 103 is then delivered to the primary fractionation column T1 as the phenol/cyclohexanone/cyclohexylbenzene feed (first mixture). By adding a small, relatively inexpensive anterior stripper column T4, one can remove a great majority of the light components prone to poisoning the hydrogenation catalyst such as benzoic acids and other C1-C8 organic acids, S-containing compounds and N-containing compounds. In addition, the lower anterior stripper effluent 103, if still found to contain catalyst poison components at unacceptably high concentrations, can be further treated by passing through a bed of anterior sorbent located inside or outside of T4 (not shown) capable of removing at least a portion of the catalyst poison components before it is being fed to the primary fractionation column T1. Alternatively, where the total concentration of the catalyst poison components in the crude mixture stream 102 is not exceedingly high, the anterior stripper distillation column T4 may be omitted, and the crude mixture stream 102 may be treated only by contacting an anterior sorbent (e.g., passing through a sorbent bed or washing with a sorbent liquid dispersion) before being fed into T1 as the first mixture. Desirably, upon treatment, concentrations of catalyst poison components capable of poisoning the hydrogenation catalyst is reduced significantly in effluent 107 compared to in feed 102. Thus, in the embodiment shown in FIG. 7, assuming the total concentration of catalyst poison components in feed 102 is Clc(cm), and the total concentration of catalyst poison components in effluent 107 is Clc(ME1), r1≤Clc(ME1)/Clc(cm)≤r2, where r1 and r2 can be, independently: 0.001, 0.002, 0.003, 0.004, 0.005, 0.006, 0.007, 0.008, 0.009, 0.01, 0.02, 0.02, 0.03, 0.04, 0.05, 0.06, 0.07, 0.08, 0.09, 0.1, 0.2, 0.3, 0.4, 0.5, as long as r1<r2. Specifically, assuming the concentration of benzoic acid in feed 102 is Cba(cm), and the total concentration of benzoic acid in effluent 107 is Cba(ME1), r1≤Cba(ME1)/Cba(cm)≤r2, where r1 and r2 can be, independently: 0.001, 0.002, 0.003, 0.004, 0.005, 0.006, 0.007, 0.008, 0.009, 0.01, 0.02, 0.02, 0.03, 0.04, 0.05, 0.06, 0.07, 0.08, 0.09, 0.1, 0.2, 0.3, 0.4, 0.5, as long as r1<r2.

Figure 8:
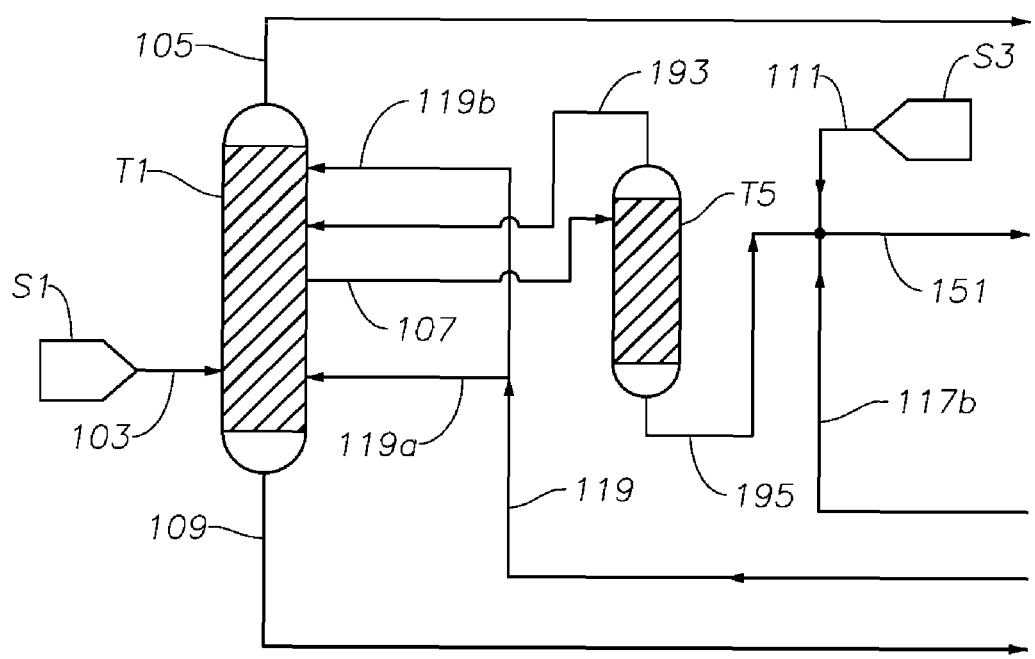
FIG. 8 is a schematic diagram showing a portion of a process/system similar to those shown in FIGS. 1 to 7, comprising a posterior stripper distillation column T5 after the primary fractionation column T1 configured for removing at least a portion of the catalyst poison components from the phenol/cyclohexanone/cyclohexylbenzene feed fed to the hydrogenation reactor to reduce or prevent catalyst poisoning in the hydrogenation reactor.

FIG. 8 shows an alternative to the configuration of FIG. 7. In this figure, instead of placing an anterior stripper distillation column T4 before the primary fractionation column T1, a posterior stripper distillation column T5 is placed behind column T1, which receives the first middle effluent 107 as a feed, produces an upper posterior stripper effluent 193 rich in catalyst poison components prone to poisoning the hydrogenation catalyst described above, which is recycled to column T1 at a location higher than the location where effluent 107 is drawn, and a lower posterior stripper effluent 195 depleted with or low in such catalyst poison components, which, together with hydrogen feeds 111 and 117b, is delivered to the hydrogenation reactor as a portion or all of the hydrogenation feed 151. It is highly likely that the upper posterior effluent 193 contains phenol at a non-negligible amount given the location on T1 at which the middle effluent 107 is drawn, and therefore, it is preferred that effluent 193 is fed back to T1 instead of combined with the first upper effluent 105 and delivered to the cyclohexanone purification column T2. In addition, the lower posterior stripper effluent 195, if still found to contain the catalyst poison components at unacceptably high concentrations, can be further treated by passing through a bed of posterior sorbent located inside or outside of T5 (not shown) capable of removing at least a portion of the catalyst poison components before it is being fed to the hydrogenation reactor R1. Alternatively, where the total concentration of the catalyst poison components in the first middle effluent 107 is not exceedingly high, the posterior stripper distillation column T5 may be omitted, and effluent 107 may be treated only by contacting a posterior sorbent (e.g., passing through a solid sorbent bed, washing by a sorbent liquid dispersion, and the like) before being fed to the hydrogenation reactor R1 as at least a portion of the hydrogenation feed. Desirably, upon treatment, concentrations of catalyst poison components capable of poisoning the hydrogenation catalyst is reduced significantly the hydrogenation feed compared to in effluent 107. Thus, in the embodiment shown in FIG. 8, assuming the total concentration of catalyst poison components in the hydrogenation feed is Clc(hf), and the total concentration of catalyst poison components in effluent 107 is Clc(ME1), $r1 \leq Clc(hf)/Clc(ME1) \leq r2$, where r1 and r2 can be, independently: 0.001, 0.002, 0.003, 0.004, 0.005, 0.006, 0.007, 0.008, 0.009, 0.01, 0.02, 0.02, 0.03, 0.04, 0.05, 0.06, 0.07, 0.08, 0.09, 0.1, 0.2, 0.3, 0.4, 0.5, as long as r1<r2. Specifically, assuming the concentration of benzoic acid in the hydrogenation feed is Cba(hf), and the total concentration of benzoic acid in effluent 107 is Cba(ME1), $r1 \leq Cba(hf)/Cba(ME1) \leq r2$, where r1 and r2 can be, independently: 0.001, 0.002, 0.003, 0.004, 0.005, 0.006, 0.007, 0.008, 0.009, 0.01, 0.02, 0.02, 0.03, 0.04, 0.05, 0.06, 0.07, 0.08, 0.09, 0.1, 0.2, 0.3, 0.4, 0.5, as long as r1<r2.

If necessary, both of the anterior catalyst poison component removing mechanism described in connection with FIG. 7 (one or both of the anterior stripper distillation column and the anterior sorbent) and the posterior catalyst poison component removing mechanism described in connection with FIG. 8 (one or both of the posterior stripper distillation column and the posterior sorbent) may be used to prevent the catalyst poison components from entering into the hydrogenation reactor(s) at an unacceptably high concentrations. The anterior and posterior sorbents can be the same or different, and may be selected from: massive nickel; activated carbon, ion exchange resins (such as strong and weak anion resins which are usually amine based), clay, kaolin, silica sorbents, alumina sorbents, molecular sieves, alkali carbonates, alkali bicarbonates, alkali hydroxides, alkaline earth carbonates, alkaline earth bicarbonates, alkaline earth hydroxides, carbonates and bicarbonates of other metals such as zinc, mixtures and combinations thereof, and the like. The sorbents may remove the catalyst poison components by physical absorption or adsorption, extraction, and/or chemical reactions. Massive nickel is particularly useful for removing S-containing and N-containing poison components.

Preferably, the hydrogenation feed thus treated by the anterior and/or posterior treatment(s) described in connection with FIG. 7 and/or FIG. 8 may comprise the catalyst poison components at a total concentration in a range from Clc(hf)1 ppm to Ccl(hf)2 ppm by weight based on the total weight of the hydrogenation feed, where Clc(hf)1 and Clc (hf)2 can be, independently, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100, as long as Clc(hf)1<Clc(hf)2. Preferably, the hydrogenation feed thus treated by the anterior and/or posterior treatment(s) described in connection with FIG. 7 and/or FIG. 8 may comprise the benzoic acid at a concentration in a range from Cba(hf)1 ppm to Cba(hf)2 ppm by weight based on the total weight of the hydrogenation feed, where Cba (hf)1 and Cba(hf)2 can be, independently, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100, as long as Clc(hf)1<Clc(hf)2.

Figure 9:
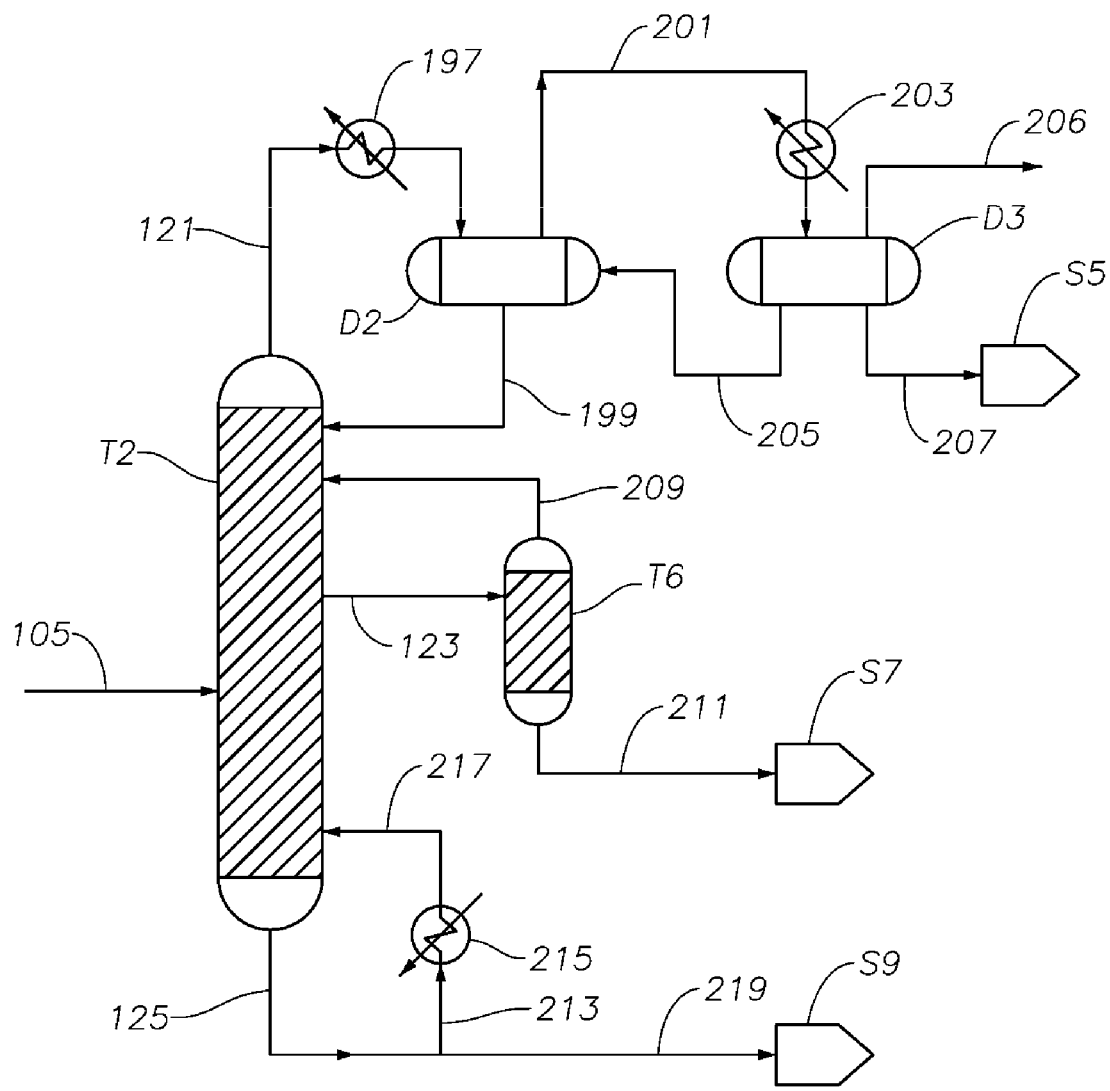
FIG. 9 is a schematic diagram showing a portion of a process/system similar to those shown in FIGS. 1 to 8, comprising a side stripper column T6 after the cyclohexanone purification column T2, configured to reduce amounts of catalyst poison components from the final cyclohexanone product.

FIG. 9 is a schematic diagram showing a portion of a process/system similar to those shown in FIGS. 1-8 comprising a side stripper column T6 after the cyclohexanone purification column T2, configured to reduce amounts of light components from the final cyclohexanone product. In this figure, the first upper effluent 105 comprising primarily cyclohexanone and light components obtained from the primary fractionation column T1 and from the upper anterior stripper effluent, if any, is delivered to cyclohexanone purification column T2, where three effluents are obtained: a second upper effluent 121 rich in light components such as water and methylcyclopentanone and depleted in cyclohexanone and cyclohexanol, a second middle effluent 123 rich in cyclohexanone and depleted in light components and cyclohexanol, and a second lower effluent 125 rich in cyclohexanol. Effluent 121 is first cooled down by a heat exchanger 197, then delivered to a separation drum D2 to obtain a liquid phase 199, which is recycled to column T2, and a vapor phase 201, which is cooled again by a heat exchanger 203, and delivered to another separation drum D3 to obtain a liquid phase which is partly recycled as stream 205 to drum D2, and partly delivered to storage S5, and a vapor phase 206 which can be purged. Effluent 123 is delivered to a side stripper T6 where the following streams are produced: a substantially pure cyclohexanone stream 211 in the vicinity of the bottom thereof, which is delivered to a storage S7; and a light component stream 209, which is recycled to the column T2 at a location above 123.

In all of the above drawings, the phenol/cyclohexanone/cyclohexylbenzene hydrogenation feed delivered to the hydrogenation reactor is wholly obtained from one or more middle effluents from primary fractionation column T1. However, it is contemplated that, additionally, a second phenol feed stream comprising phenol at a concentration not lower than the feed obtained from column T1 can be fed to the hydrogenation reactor, either independently and separately or after being combined with the feed obtained from column T1 and/or hydrogen feed. For example, the second phenol stream may comprise substantially pure phenol having a phenol concentration, based on its total weight, of at least Cphol(f2) wt %, where Cphol(f2) can be, e.g., 80, 82, 84, 85, 86, 88, 90, 91, 92, 93, 94, 95, 96, 97, 98, 99, 99.5, 99.8, or even 99.9.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

The present invention includes one or more of the following non-limiting aspects and/or embodiments.

EA1. A process for making cyclohexanone, the process comprising:

(I) feeding a first mixture comprising cyclohexanone, phenol, cyclohexylbenzene, and a catalyst poison component into a first distillation column;

(II) obtaining from the first distillation column:

a first upper effluent comprising cyclohexanone at a concentration higher than the first mixture;

a first middle effluent comprising cyclohexanone, phenol at a concentration higher than the first mixture, cyclohexylbenzene, bicyclohexane, and a portion of the catalyst poison component; and a first lower effluent comprising cyclohexylbenzene at a concentration higher than the first mixture;

(III) removing at least a portion of the catalyst poison component from the first middle effluent to obtain a hydrogenation feed;

(IV) feeding at least a portion of the hydrogenation feed and hydrogen into a hydrogenation reaction zone where phenol reacts with hydrogen in the presence of a hydrogenation catalyst under hydrogenation reaction conditions to obtain a hydrogenation reaction product comprising cyclohexanone at a concentration higher than the hydrogenation feed, phenol at a concentration lower than the hydrogenation feed, cyclohexylbenzene, and bicyclohexane; and (V) feeding at least a portion of the hydrogenation reaction product into the first distillation column, wherein the hydrogenation catalyst poison component is capable of reducing the activity of the hydrogenation catalyst if the catalyst poison component is allowed to contact the hydrogenation catalyst under the hydrogenation reaction conditions.

EA2. The process of EA1, wherein the catalyst poison component comprises a light component having a normal boiling point lower than cyclohexanone.

EA3. The process of EA1 or EA2, wherein the catalyst poison component comprises at least one of the following: (i) methylcyclopentanone; (ii) N-containing compounds; (iii) S-containing compounds; and (iv) hydrocarbons comprising 4 to 8 carbon atoms; and (v) oxygenates of hydrocarbons comprising 1 to 12 carbon atoms.

EA4. The process of EA1, wherein step (III) comprises:

(IIIa) feeding the first middle effluent into a posterior stripper distillation column;

(IIIb) obtaining from the posterior stripper distillation column:

an upper posterior stripper effluent comprising cyclohexanone and a portion of the catalyst poison component; and a lower posterior stripper effluent comprising phenol, cyclohexylbenzene and bicyclohexane;

(IIIc) providing at least a portion of the lower posterior stripper effluent as at least a portion of the hydrogenation feed.

EA5. The process of any of EA1 to EA4, wherein step (III) comprises:

(IIId) contacting at least a portion of the first middle effluent with a posterior sorbent capable of removing at least a portion of the catalyst poison component to obtain the hydrogenation feed.

EA6. The process of EA5, wherein all steps (IIIa), (IIIb), (IIIc), and (IIId) are carried out, and at least a portion of the lower posterior stripper effluent is passed through a bed of the posterior sorbent in step (IIId).

EA7. The process of any of EA1 to EA6, wherein the concentration of the catalyst poison component in the hydrogenation feed is at most 100 ppm by weight based on the total weight of the hydrogenation feed.

EA8. The process of any of EA1 to EA7, wherein the concentration of the catalyst poison component in the first middle effluent is in a range from 1 ppm to 10,000 ppm by weight based on the total weight of the first middle effluent.

EA9. The process of any of EA1 to EA8, wherein the concentration of the catalyst poison component in the hydrogenation feed based on the total weight of the hydrogenation feed is at most 10% of the concentration of the catalyst poison component in the first middle effluent based on the total weight of the first middle effluent.

EA10. The process of any of EA1 to EA9, wherein the hydrogenation feed comprises:

cyclohexanone at a concentration in a range from 1 wt % to 50 wt %;

phenol at a concentration in a range from 10 wt % to 80 wt %;

cyclohexylbenzene at a concentration in a range from 0.001 wt % to 30 wt %; and bicyclohexane at a concentration in a range from 0.001 wt % to 30 wt %, the percentages being based on the total weight of the hydrogenation feed.

EA11. The process of any of EA1 to EA10, wherein the first mixture comprises:

cyclohexanone at a concentration in a range from 10 wt % to 90 wt %;

phenol at a concentration in a range from 10 wt % to 80 wt %; and cyclohexylbenzene at a concentration in a range from 0.001 wt % to 75 wt %;

the percentages being based on the total weight of the first mixture.

EA12. The process of any of EA1 to EA11, wherein in step (IV), the hydrogenation catalyst comprises (i) a hydrogenation metal selected from Fe, Co, Ni, Ru, Rh, Pd, Ag, Re, Os, Ir, and Pt at a concentration in a range from 0.001 wt % to 5.0 wt %, based on the total weight of the catalyst; and (ii) an inorganic support material selected from activated carbon, $Al_2O_3$, $Ga_2O_3$, $SiO_2$, $GeO_2$, $SnO$, $SnO_2$, $TiO_2$, $ZrO_2$, $Sc_2O_3$, $Y_2O_3$, alkali metal oxides, alkaline earth metal oxides, and mixtures, combinations, complexes and compounds thereof.

EA13. The process of any of EA1 to EA12, wherein the first upper effluent further comprises cyclohexanol, and the process further comprises:

(VI) feeding at least a portion of the first upper effluent into a second distillation column; and (VII) obtaining the following from the second distillation column:

a second upper effluent comprising cyclohexanone at a concentration higher than the first upper effluent;

a third upper effluent at a location above the second upper effluent, the third upper effluent comprising components having normal boiling points lower than that of cyclohexanone; and a second lower effluent comprising cyclohexanone at a concentration lower than the first upper effluent, and cyclohexanol at a concentration higher than the first upper effluent.

EA14. The process of EA13, wherein at least a portion of the upper posterior stripper effluent is fed into the second distillation column.

EA15. The process of any of EA1 to EA14, wherein step (I) comprises:

(Ia) feeding a crude mixture comprising cyclohexanone, phenol, cyclohexylbenzene, and the catalyst poison component into an anterior stripper distillation column;

(Ib) obtaining from the anterior stripper distillation column:

an upper anterior stripper effluent comprising cyclohexanone and a portion of the catalyst poison component; and a lower anterior stripper effluent comprising cyclohexanone, phenol, cyclohexylbenzene, and a portion of the catalyst poison component; and (Ic) feeding at least a portion of the lower anterior stripper effluent to the first distillation column as the first mixture.

EA16. The process of EA15, wherein at least a portion of the lower anterior stripper effluent is contacted with an anterior sorbent capable of removing at least a portion of the catalyst poison component before being fed to the first distillation column as the first mixture in step (Ic).

EA17. The process of EA15 or EA16, wherein at least a portion of the upper anterior stripper effluent is fed to the second distillation column.

EA18. The process of any of EA5 to EA17, wherein the posterior sorbent and/or the anterior sorbent are selected from: activated carbon, massive nickel, ion exchange resins, clay, kaolin, silica sorbents, alumina sorbents, molecular sieves, carbonates, bicarbonates and hydroxides of alkali metals, alkaline earth metals and transition metals, and mixtures and combinations thereof.

EA19. The process of any of EA1 to EA18, wherein in step (IV), hydrogen and phenol are fed into the hydrogenation reaction zone at a hydrogen to phenol molar ratio in a range from 1.0 to 10.

EA20. The process of any of EA1 to EA19, wherein the first mixture in step (I) is obtained by a cleavage process comprising:

(I-A) contacting a cleavage feed mixture comprising 1-phenyl-1-cyclohexane-hydroperoxide and cyclohexylbenzene with an acid catalyst in a cleavage reactor to obtain a cleavage reaction product; and (I-B) adding a basic material into the cleavage reaction product to obtain the first mixture.

EA21. The process of EA20, wherein the cleavage feed mixture is obtained by:

(I-A-1) contacting benzene with hydrogen in the presence of a hydroalkylation catalyst under hydroalkylation conditions to produce a hydroalkylation product mixture comprising cyclohexylbenzene;

(I-A-2) contacting the cyclohexylbenzene with oxygen in the presence of a catalyst to produce an oxidation reaction product mixture comprising 1-phenyl-1-cyclohexane-hydroperoxide; and (I-A-3) providing the cleavage feed mixture from the oxidation reaction product mixture.

EB1. A process for making cyclohexanone, the process comprising:

(I) feeding a first mixture comprising cyclohexanone, phenol, cyclohexylbenzene, and a catalyst poison component into a first distillation column;

(II) obtaining from the first distillation column:

a first upper effluent comprising cyclohexanone at a concentration higher than the first mixture;

a first middle effluent comprising cyclohexanone, phenol at a concentration higher than the first mixture, cyclohexylbenzene, bicyclohexane, and a portion of the catalyst poison component; and a first lower effluent comprising cyclohexylbenzene at a concentration higher than the first mixture;

(III) removing at least a portion of the catalyst poison component from the first middle effluent to obtain a hydrogenation feed;

(IV) feeding at least a portion of the hydrogenation feed and hydrogen into a hydrogenation reaction zone where phenol reacts with hydrogen in the presence of a hydrogenation catalyst under hydrogenation reaction conditions to obtain a hydrogenation reaction product comprising cyclohexanone at a concentration higher than the hydrogenation feed, phenol at a concentration lower than the hydrogenation feed, cyclohexylbenzene, and bicyclohexane; and (V) feeding at least a portion of the hydrogenation reaction product into the first distillation column, wherein the hydrogenation catalyst poison component is capable of reducing the activity of the hydrogenation catalyst if the catalyst poison component is allowed to contact the hydrogenation catalyst under the hydrogenation reaction conditions.

EB2. The process of EB1, wherein step (I) comprises:

(Ia) feeding the crude mixture into an anterior stripper distillation column;

(Ib) obtaining from the anterior stripper distillation column:

an upper anterior stripper effluent comprising cyclohexanone and a portion of the catalyst poison component; and a lower anterior stripper effluent comprising phenol and cyclohexylbenzene; and (Ic) providing at least a portion of the lower anterior stripper effluent as at least a portion of the first mixture.

EB3. The process of EB2, wherein in step (I), at least a portion of the lower anterior stripper effluent is contacted with an anterior sorbent capable of removing at least a portion of the catalyst poison component before being provided as the first mixture in step (Ic).

EB4. The process of any of EB1 to EB3, wherein in step (I), at least a portion of the crude mixture is treated by contacting with an anterior sorbent capable of removing at least a portion of the catalyst poison component before being bed to the first distillation column as the first mixture.

EB5. The process of any of EB1 to EB4, wherein the catalyst poison component comprises a light component having a normal boiling point lower than cyclohexanone.

EB6. The process of any of EB1 to EB5, wherein the catalyst poison component comprises at least one of the following: (i) methylcyclopentanone; (ii) N-containing compounds; (iii) S-containing compounds; and (iv) hydrocarbons comprising 4 to 8 carbon atoms; and (v) oxygenates of hydrocarbons comprising 1 to 12 carbon atoms.

EB7. The process of any of EB1 to EB6, wherein the concentration of the catalyst poison component in the crude mixture is in a range from 1 ppm to 10,000 ppm by weight based on the total weight of the crude mixture.

EB8. The process of any of EB1 to EB7, wherein the concentration of the catalyst poison component in the first middle effluent is in a range from 2 ppm to 1,000 ppm by weight based on the total weight of the first middle effluent.

EB9. The process of any of EB1 to EB8, wherein the concentration of the catalyst poison component in the hydrogenation feed is at most 100 ppm by weight based on the total weight of the hydrogenation feed.

EB10. The process of any of EB1 to EB9, wherein the concentration of the catalyst poison component in the hydrogenation feed based on the total weight of the hydrogenation feed is at most 10% of the concentration of the catalyst poison component in the crude mixture based on the total weight of the crude mixture.

EB11. The process of any of EB1 to EB10, wherein the hydrogenation feed comprises:
cyclohexanone at a concentration in a range from 1 wt % to 50 wt %;
phenol at a concentration in a range from 10 wt % to 80 wt %;
cyclohexylbenzene at a concentration in a range from 0.001 wt % to 30 wt %; and
bicyclohexane at a concentration in a range from 0.001 wt % to 30 wt %,
the percentages being based on the total weight of the hydrogenation feed.

EB12. The process of any of EB1 to EB11, wherein the crude mixture comprises:
cyclohexanone at a concentration in a range from 10 wt % to 90 wt %;
phenol at a concentration in a range from 10 wt % to 80 wt %; and
cyclohexylbenzene at a concentration in a range from 0.001 wt % to 75 wt %;
the percentages being based on the total weight of the crude mixture.

EB13. The process of any of EB1 to EB12, wherein in step (IV), the hydrogenation catalyst comprises (i) a hydrogenation metal selected from Fe, Co, Ni, Ru, Rh, Pd, Ag, Re, Os, Ir, and Pt at a concentration in a range from 0.001 wt % to 5.0 wt %, based on the total weight of the catalyst; and (ii) an inorganic support material selected from activated carbon, $Al_2O_3$, $Ga_2O_3$, $SiO_2$, $GeO_2$, $SnO$, $SnO_2$, $TiO_2$, $ZrO_2$, $Sc_2O_3$, $Y_2O_3$, alkali metal oxides, alkaline earth metal oxides, and mixtures, combinations, complexes and compounds thereof.

EB14. The process of any of EB1 to EB13, wherein the first upper effluent further comprises cyclohexanol, and the process further comprises:
(VI) feeding at least a portion of the first upper effluent into a second distillation column; and
(VII) obtaining the following from the second distillation column:
a second upper effluent comprising cyclohexanone at a concentration higher than the first upper effluent;
a third upper effluent at a location above the second upper effluent, the third upper effluent comprising components having normal boiling points lower than that of cyclohexanone; and
a second lower effluent comprising cyclohexanone at a concentration lower than the first upper effluent, and cyclohexanol at a concentration higher than the first upper effluent.

EB15. The process of EB14, wherein at least a portion of the upper anterior stripper effluent is fed into the second distillation column.

EB16. The process of any of EB1 to EB15, wherein step (III) comprises:
(IIIa) feeding the first middle effluent into a posterior stripper distillation column;

(IIIb) obtaining from the posterior stripper distillation column:
an upper posterior stripper effluent comprising cyclohexanone and a portion of the catalyst poison component; and
a lower posterior stripper effluent comprising phenol, cyclohexylbenzene and bicyclohexane;
(IIIc) providing at least a portion of the lower posterior stripper effluent as at least a portion of the hydrogenation feed.

EB17. The process of any of EB1 to EB16, wherein step (III) comprises:
(IIId) contacting at least a portion of the first middle effluent with a posterior sorbent capable of removing at least a portion of the catalyst poison component to obtain the hydrogenation feed.

EB18. The process of EB17, wherein all steps (IIIa), (IIIb), (IIIc), and (IIId) are carried out, and at least a portion of the lower posterior stripper effluent is passed through a bed of the posterior sorbent in step (IIId).

EB19. The process of any of EB1 to EB18, wherein at least a portion of the upper posterior stripper effluent is fed into the second distillation column.

EB20. The process of any of EB1 to EB19, wherein the posterior sorbent and/or the anterior sorbent are selected from: activated carbon, a molecular sieve, clay, silica, alumina, and mixtures and combinations thereof.

EB21. The process of any of EB1 to EB20, wherein in step (IV), hydrogen and phenol are fed into the hydrogenation reaction zone at a hydrogen to phenol molar ratio in a range from 1.0 to 10.

EB22. The process of any of EB1 to EB21, wherein the first mixture in step (I) is obtained by a cleavage process comprising:
(I-A) contacting a cleavage feed mixture comprising 1-phenyl-1-cyclohexane-hydroperoxide and cyclohexylbenzene with an acid catalyst in a cleavage reactor to obtain a cleavage reaction product; and
(I-B) adding a basic material into the cleavage reaction product to obtain the first mixture.

EB23. The process of EB22, wherein the cleavage feed mixture is obtained by:
(I-A-1) contacting benzene with hydrogen in the presence of a hydroalkylation catalyst under hydroalkylation conditions to produce a hydroalkylation product mixture comprising cyclohexylbenzene;
(I-A-2) contacting the cyclohexylbenzene with oxygen in the presence of a catalyst to produce an oxidation reaction product mixture comprising 1-phenyl-1-cyclohexane-hydroperoxide; and
(I-A-3) providing the cleavage feed mixture from the oxidation reaction product mixture.

The invention claimed is:
1. A process for making cyclohexanone, the process comprising the following steps:
(I) feeding a first mixture comprising cyclohexanone, phenol, cyclohexylbenzene, and a catalyst poison component into a first distillation column;
(II) obtaining from the first distillation column:
a first upper effluent comprising cyclohexanone at a concentration higher than the first mixture and a portion of the catalyst poison component;
a first middle effluent comprising cyclohexanone, phenol at a concentration higher than the first mixture, cyclohexylbenzene, bicyclohexane, and a portion of the catalyst poison component; and a first lower effluent comprising cyclohexylbenzene at a concentration higher than the first mixture;

(III) removing at least a portion of the catalyst poison component from the first middle effluent to obtain a hydrogenation feed;

(IV) feeding at least a portion of the hydrogenation feed and hydrogen into a hydrogenation reaction zone where phenol reacts with hydrogen in the presence of a hydrogenation catalyst under hydrogenation reaction conditions to obtain a hydrogenation reaction product comprising cyclohexanone at a concentration higher than the hydrogenation feed, phenol at a concentration lower than the hydrogenation feed, cyclohexylbenzene, and bicyclohexane; and (V) feeding at least a portion of the hydrogenation reaction product into the first distillation column, wherein the hydrogenation catalyst poison component is capable of reducing the activity of the hydrogenation catalyst if the catalyst poison component is allowed to contact the hydrogenation catalyst under the hydrogenation reaction conditions.

2. The process of claim 1, wherein the catalyst poison component comprises a light component having a normal boiling point lower than cyclohexanone.

3. The process of claim 1, wherein the catalyst poison component comprises at least one of the following: (i) methylcyclopentanone; (ii) N-containing compounds; (iii) S-containing compounds; (iv) hydrocarbons comprising 4 to 8 carbon atoms; and (v) oxygenates of hydrocarbons comprising 1 to 12 carbon atoms.

4. The process of claim 1, wherein step (III) comprises:
(IIIa) feeding the first middle effluent into a posterior stripper distillation column;
(IIIb) obtaining from the posterior stripper distillation column:
an upper posterior stripper effluent comprising cyclohexanone and a portion of the catalyst poison component; and
a lower posterior stripper effluent comprising phenol, cyclohexylbenzene and bicyclohexane;
(IIIc) providing at least a portion of the lower posterior stripper effluent as at least a portion of the hydrogenation feed.

5. The process of claim 1, wherein step (III) comprises:
(IIId) contacting at least a portion of the first middle effluent with a posterior sorbent capable of removing at least a portion of the catalyst poison component to obtain the hydrogenation feed.

6. The process of claim 1, wherein the concentration of the catalyst poison component in the hydrogenation feed is at most 100 ppm by weight based on the total weight of the hydrogenation feed.

7. The process of claim 1, wherein the concentration of the catalyst poison component in the first middle effluent is in a range from 2 ppm to 10,000 ppm by weight based on the total weight of the first middle effluent.

8. The process of claim 1, wherein the concentration of the catalyst poison component in the hydrogenation feed based on the total weight of the hydrogenation feed is at most 10% of the concentration of the catalyst poison component in the first middle effluent based on the total weight of the first middle effluent.

9. The process of claim 4, wherein the first upper effluent further comprises cyclohexanol, and the process further comprises:
(VI) feeding at least a portion of the first upper effluent into a second distillation column; and (VII) obtaining the following from the second distillation column:
a second upper effluent comprising cyclohexanone at a concentration higher than the first upper effluent;
a third upper effluent at a location above the second upper effluent, the third upper effluent comprising components having normal boiling points lower than that of cyclohexanone; and
a second lower effluent comprising cyclohexanone at a concentration lower than the first upper effluent, and cyclohexanol at a concentration higher than the first upper effluent.

10. The process of claim 9, wherein at least a portion of the upper posterior stripper effluent is fed into the second distillation column.

11. The process of claim 5, wherein the posterior sorbent is selected from: activated carbon, massive nickel, ion exchange resins, clay, kaolin, silica sorbents, alumina sorbents, molecular sieves, carbonates, bicarbonates and hydroxides of alkali metals, alkaline earth metals and transition metals, and mixtures and combinations thereof.

12. A process for making cyclohexanone, the process comprising:
(I) feeding a first mixture comprising cyclohexanone, phenol, and cyclohexylbenzene into a first distillation column, wherein the first mixture is provided by removing at least a portion of a catalyst poison component from a crude mixture comprising cyclohexanone, phenol, cyclohexylbenzene, and the catalyst poison component;
(II) obtaining from the first distillation column:
a first upper effluent comprising cyclohexanone at a concentration higher than the first mixture;
a first middle effluent comprising cyclohexanone, phenol at a concentration higher than the first mixture, cyclohexylbenzene, bicyclohexane, and optionally a portion of the catalyst poison component; and
a first lower effluent comprising cyclohexylbenzene at a concentration higher than the first mixture;
(III) providing a hydrogenation feed from at least a portion of the first middle effluent;
(IV) feeding at least a portion of the hydrogenation feed and hydrogen into a hydrogenation reaction zone where phenol reacts with hydrogen in the presence of a hydrogenation catalyst under hydrogenation reaction conditions to obtain a hydrogenation reaction product comprising cyclohexanone at a concentration higher than the hydrogenation feed, phenol at a concentration lower than the hydrogenation feed, cyclohexylbenzene, and bicyclohexane; and
(V) feeding at least a portion of the hydrogenation reaction product into the first distillation column,
wherein the hydrogenation catalyst poison component is capable of reducing the activity of the hydrogenation catalyst if the catalyst poison component is allowed to contact the hydrogenation catalyst under the hydrogenation reaction conditions.

13. The process of claim 12, wherein step (I) comprises:
(Ia) feeding the crude mixture into an anterior stripper distillation column;
(Ib) obtaining from the anterior stripper distillation column;
an upper anterior stripper effluent comprising cyclohexanone and the catalyst poison component; and
a lower anterior stripper effluent comprising phenol and cyclohexylbenzene; and (Ic) providing at least a portion of the lower anterior stripper effluent as at least a portion of the first mixture.

14. The process of claim 13, wherein the first upper effluent further comprises cyclohexanol, and the process further comprises:
(VI) feeding at least a portion of the first upper effluent into a second distillation column; and
(VII) obtaining the following from the second distillation column:
a second upper effluent comprising cyclohexanone at a concentration higher than the first upper effluent;
a third upper effluent at a location above the second upper effluent, the third upper effluent comprising components having normal boiling points lower than that of cyclohexanone; and
a second lower effluent comprising cyclohexanone at a concentration lower than the first upper effluent, and cyclohexanol at a concentration higher than the first upper effluent.

15. The process of claim 14, wherein at least a portion of the upper anterior stripper effluent is fed into the second distillation column.

16. The process of claim 13, wherein in step (I), at least a portion of the lower anterior stripper effluent is contacted with an anterior sorbent capable of removing at least a portion of the catalyst poison component before being provided as the first mixture in step (Ic).

17. The process of claim 12, wherein in step (I), at least a portion of the crude mixture is treated by contacting with an anterior sorbent capable of removing at least a portion of the catalyst poison component before being bed to the first distillation column as the first mixture.

18. The process of claim 12, wherein the catalyst poison component comprises at least one of the following: (i) methylcyclopentanone; (ii) N-containing compounds; (iii) S-containing compounds; (iv) hydrocarbons comprising 4 to 8 carbon atoms; and (v) oxygenates of hydrocarbons comprising 1 to 12 carbon atoms.

19. The process of claim 12, wherein the concentration of the catalyst poison component in the first middle effluent is in a range from 2 ppm to 1,000 ppm by weight based on the total weight of the hydrogenation feed.

20. The process of claim 12, wherein the concentration of the catalyst poison component in the hydrogenation feed is at most 100 ppm by weight based on the total weight of the hydrogenation feed.

21. The process of claim 12, wherein the concentration of the catalyst poison component in the hydrogenation feed based on the total weight of the hydrogenation feed is at most 10% of the concentration of the catalyst poison component in the crude mixture based on the total weight of the crude mixture.

22. The process of claim 12, wherein step (III) comprises:
(IIIa) feeding the first middle effluent into a posterior stripper distillation column;
(IIIb) obtaining from the posterior stripper distillation column:
an upper posterior stripper effluent comprising cyclohexanone and a portion of the catalyst poison component; and
a lower posterior stripper effluent comprising phenol, cyclohexylbenzene and bicyclohexane;
(IIIc) providing at least a portion of the lower posterior stripper effluent as at least a portion of the hydrogenation feed.

23. The process of claim 12, wherein step (III) comprises:
(IIId) contacting at least a portion of the first middle effluent with a posterior sorbent capable of removing at least a portion of the catalyst poison component to obtain the hydrogenation feed.

24. The process of claim 12, wherein at least a portion of the upper posterior stripper effluent is fed into the first distillation column at a location higher than the first middle effluent.

25. The process of claim 23, wherein the posterior sorbent and/or the anterior sorbent are selected from: activated carbon, massive nickel, ion exchange resins, clay, kaolin, silica sorbents, alumina sorbents, molecular sieves, carbonates, bicarbonates and hydroxides of alkali metals, alkaline earth metals and transition metals, and mixtures and combinations thereof.

* * * * *